US011488361B1

(12) United States Patent
Ng et al.

(10) Patent No.: US 11,488,361 B1
(45) Date of Patent: Nov. 1, 2022

(54) SYSTEMS AND METHODS FOR CALIBRATING WEARABLES BASED ON IMPEDANCE LEVELS OF USERS' SKIN SURFACES

(71) Applicant: META PLATFORMS TECHNOLOGIES, LLC, Menlo Park, CA (US)

(72) Inventors: Shiu Sang Ng, Kirkland, WA (US); Yanjun Ma, Oro Valley, CA (US); Wolf Kienzle, Seattle, WA (US); Hrvoje Benko, Seattle, WA (US)

(73) Assignee: Meta Platforms Technologies, LLC, Menlo Park, CA (US)

( * ) Notice: Subject to any disclaimer, the term of this patent is extended or adjusted under 35 U.S.C. 154(b) by 0 days.

(21) Appl. No.: 16/526,830

(22) Filed: Jul. 30, 2019

Related U.S. Application Data

(60) Provisional application No. 62/806,754, filed on Feb. 15, 2019.

(51) Int. Cl.
  *A61B 5/00*      (2006.01)
  *A61B 5/145*     (2006.01)
  *G06T 19/00*     (2011.01)
  *A61B 5/0531*    (2021.01)

(52) U.S. Cl.
  CPC ............ *G06T 19/006* (2013.01); *A61B 5/681* (2013.01); *A61B 5/0531* (2013.01); *A61B 5/6821* (2013.01)

(58) Field of Classification Search
  CPC .................................................. A61B 5/0531
  USPC ......................................................... 345/633
  See application file for complete search history.

(56) References Cited

U.S. PATENT DOCUMENTS

| | | | | |
|---|---|---|---|---|
| 5,067,478 A | * | 11/1991 | Berlant | A61N 1/322 601/15 |
| 6,428,484 B1 | * | 8/2002 | Battmer | A61B 5/24 600/554 |
| 6,517,482 B1 | * | 2/2003 | Elden | A61B 5/14532 600/309 |

(Continued)

OTHER PUBLICATIONS

"A New Method for Non-Invasive Measurement of Skin in the Low Frequency Range" Min Soo Kim et al., Department of Internal Medicine, School of Medicine, year 2010.*

(Continued)

*Primary Examiner* — Javid A Amini
(74) *Attorney, Agent, or Firm* — FisherBroyles, LLP

(57) ABSTRACT

The disclosed wearable may include (1) a plurality of electrodes dimensioned to interface with a skin surface of a user of an artificial reality system, wherein the electrodes are spaced a known distance from one another, (2) a signal generator communicatively coupled to one of the electrodes, wherein the signal generator injects a test signal into the skin surface of the user via the one of the electrodes, (3) at least one sensor communicatively coupled to another one of the electrodes, wherein the sensor measures the test signal as received by the another one of the electrodes, and (4) at least one processing device communicatively coupled to the sensor, wherein the processing device determines a current impedance of the skin surface based at least in part on the known distance and the measurement of the test signal. Various other systems and methods are also disclosed.

18 Claims, 16 Drawing Sheets

(56) References Cited

U.S. PATENT DOCUMENTS

| | | | | |
|---|---|---|---|---|
| 7,084,642 B2* | 8/2006 | Gozzini | G06K 9/0002 | 324/663 |
| 7,474,917 B2* | 1/2009 | Jang | A61B 5/0531 | 600/547 |
| 7,848,798 B2* | 12/2010 | Martinsen | A61B 5/442 | 600/547 |
| 7,865,236 B2* | 1/2011 | Cory | A61B 5/4041 | 600/547 |
| 9,060,700 B2* | 6/2015 | Cho | A61B 5/6838 | |
| 10,335,572 B1* | 7/2019 | Kumar | G06F 3/0304 | |
| 2001/0044573 A1* | 11/2001 | Manoli | A61B 5/6804 | 600/383 |
| 2002/0095194 A1* | 7/2002 | Charvin | A61B 5/121 | 607/55 |
| 2003/0208113 A1* | 11/2003 | Mault | A61B 5/14532 | 600/316 |
| 2004/0236268 A1* | 11/2004 | Mitragotri | A61M 37/0092 | 604/20 |
| 2007/0060802 A1* | 3/2007 | Ghevondian | G16H 40/67 | 600/301 |
| 2007/0183936 A1* | 8/2007 | Newsam | G01N 33/5082 | 422/400 |
| 2009/0118666 A1* | 5/2009 | Blomqvist | A61B 5/14535 | 604/66 |
| 2009/0171236 A1* | 7/2009 | Davies | A61B 6/482 | 600/547 |
| 2009/0264792 A1* | 10/2009 | Mazar | A61B 5/259 | 600/547 |
| 2009/0281539 A1* | 11/2009 | Selig | A61B 18/16 | 606/41 |
| 2010/0234701 A1* | 9/2010 | Cho | A61B 5/14552 | 600/301 |
| 2010/0331711 A1* | 12/2010 | Krauss | A61B 5/352 | 600/509 |
| 2011/0227856 A1* | 9/2011 | Corroy | H04B 13/005 | 345/173 |
| 2011/0251817 A1* | 10/2011 | Burns | A61B 5/0531 | 702/104 |
| 2012/0016210 A1* | 1/2012 | Kim | A61B 5/6843 | 600/301 |
| 2012/0323134 A1* | 12/2012 | Cory | A61B 5/0536 | 600/547 |
| 2014/0051941 A1* | 2/2014 | Messerschmidt | A61B 5/02416 | 600/301 |
| 2014/0121658 A1* | 5/2014 | Cosman, Jr. | A61B 18/1477 | 606/33 |
| 2015/0133911 A1* | 5/2015 | Batchelor | A61B 18/1206 | 606/34 |
| 2015/0142080 A1* | 5/2015 | Maxwell | A61N 1/36031 | 607/59 |
| 2015/0177891 A1* | 6/2015 | Karkkainen | G06F 3/045 | 345/174 |
| 2015/0186039 A1* | 7/2015 | Ide | H04N 9/3194 | 345/168 |
| 2016/0007878 A1* | 1/2016 | Leuthardt | A61B 5/6825 | 600/301 |
| 2016/0012749 A1* | 1/2016 | Connor | A61B 5/00 | 600/13 |
| 2016/0018944 A1* | 1/2016 | Kim | G06F 3/017 | 345/174 |
| 2016/0198996 A1* | 7/2016 | Dullen | A61B 5/4824 | 600/301 |
| 2016/0287127 A1* | 10/2016 | Kesinger | A61B 5/6806 | |
| 2016/0338639 A1* | 11/2016 | Myers | A61B 5/0531 | |
| 2017/0049352 A1* | 2/2017 | Mirov | A61B 5/0533 | |
| 2017/0124374 A1* | 5/2017 | Rowe | G06K 9/00087 | |
| 2017/0131891 A1 | 5/2017 | Novet | | |
| 2017/0323481 A1* | 11/2017 | Tran | H04N 5/23212 | |
| 2018/0081439 A1* | 3/2018 | Daniels | G06F 3/015 | |
| 2018/0368701 A1* | 12/2018 | Vule | A61B 5/02427 | |
| 2019/0121522 A1 | 4/2019 | Davis et al. | | |
| 2019/0212828 A1 | 7/2019 | Kin et al. | | |
| 2019/0247650 A1* | 8/2019 | Tran | A61N 1/025 | |
| 2019/0342637 A1* | 11/2019 | Halac | A61B 5/14546 | |
| 2019/0365275 A1* | 12/2019 | Uehara | A61B 5/443 | |
| 2019/0369807 A1 | 12/2019 | Fujiwara | | |
| 2020/0000355 A1* | 1/2020 | Khair | A61N 1/36103 | |
| 2020/0008299 A1* | 1/2020 | Tran | H05K 1/189 | |
| 2020/0077892 A1* | 3/2020 | Tran | G08B 25/016 | |
| 2020/0187823 A1* | 6/2020 | Lepak | A61B 5/0531 | |
| 2021/0169364 A1* | 6/2021 | Han | A61B 5/4266 | |

OTHER PUBLICATIONS

Year 1999, IEEE "Model for human skin impedance during surface functional neuromuscular stimulation" Stephen Dorgan et al.*

Year 1983, Medical & Biological Engineering & Computing "Impedance measurement of individual skin surface electrodes", S. Grimnes.*

Year 2015, ProQuest "Dynamic Impedance Model of the Skin-Electrode Interface for Transcutaneous Electrical Stimulation" José Luis Vargas Luna et al.*

"A Model for Human Skin Impedance During Surface Functional Neuromuscular Stimulation" Stephen J. Dorgan et al., IEEE transactions on rehabilitation engineering, vol. 7, No. 3, Sep. 1999.*

Method for Body Impedance Measurement, R. Copmdean, R. Holonec, F. Dragan, and C. Muresan, , 6th International Conference on Advancements of Medicine and Health Care through Technology; Oct. 17-20, 2018.*

The measurement principle for evaluating the performance of drugs and cosmetics by skin impedance, Y. Yamamoto T. Yamamoto, M~ed. & Biol. Eng. & Comput., 1978, 16, 623-632.*

Important Factors in Surface EMG Measurement, By Dr. Scott Day, 2002.*

* cited by examiner

SYSTEMS AND METHODS FOR CALIBRATING WEARABLES BASED ON IMPEDANCE LEVELS OF USERS' SKIN SURFACES

CROSS REFERENCE TO RELATED APPLICATION

This application claims the benefit of U.S. Provisional Application No. 62/806,754, filed on Feb. 15, 2019, the disclosure of which is incorporated, in its entirety, by this reference.

BRIEF DESCRIPTION OF DRAWINGS AND APPENDIX

The accompanying Drawings illustrate a number of exemplary embodiments and are parts of the specification. Together with the following description, the Drawings demonstrate and explain various principles of the instant disclosure.

Figure 1:
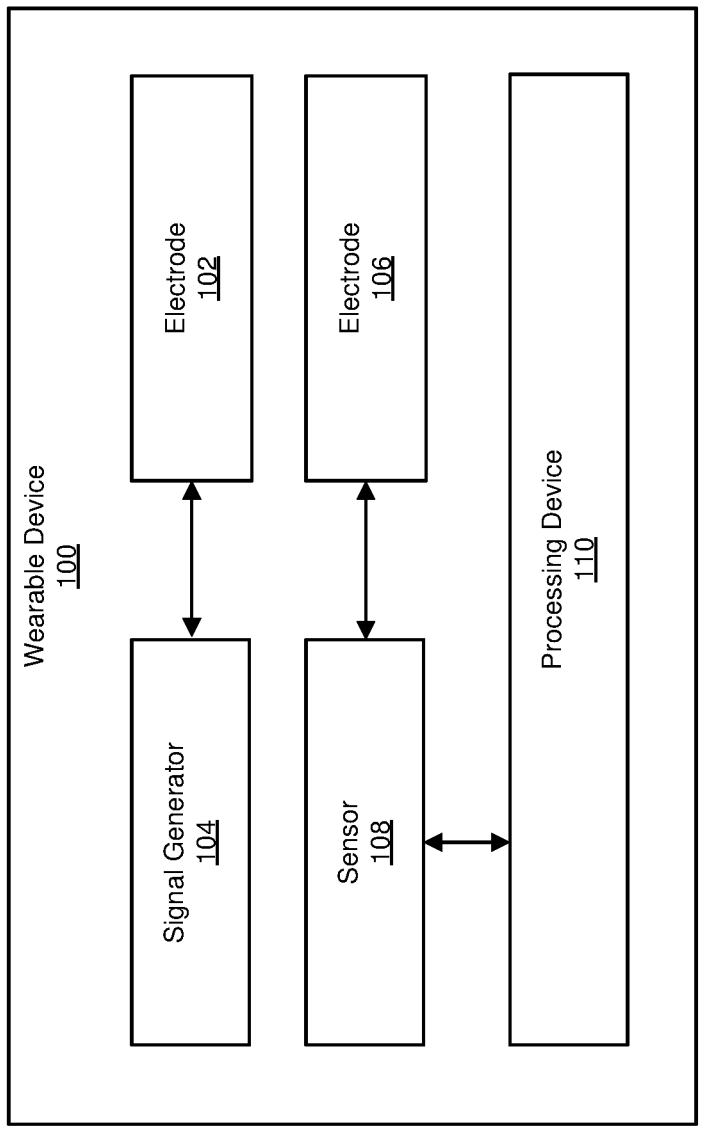
FIG. 1 is a block diagram of an exemplary wearable that may be used in connection with embodiments of this disclosure.

While the exemplary embodiments described herein are susceptible to various modifications and alternative forms, specific embodiments have been shown by way of example in the drawings and will be described in detail herein. However, the exemplary embodiments described herein are not intended to be limited to the particular forms disclosed. Rather, the instant disclosure covers all modifications, combinations, equivalents, and alternatives falling within this disclosure.

DETAILED DESCRIPTION OF EXEMPLARY EMBODIMENTS

The present disclosure is generally directed to systems and methods for calibrating wearables based on impedance levels of users' skin surfaces. As will be explained in greater detail below, these systems and methods may provide numerous features and benefits.

Artificial reality often provides a rich, immersive experience in which users are able to interact with virtual objects and/or environments in one way or another. In this context, artificial reality may constitute a form of reality that has been altered by virtual objects for presentation to a user. Such artificial reality may include and/or represent virtual reality, augmented reality, mixed reality, hybrid reality, or some combination and/or variation one or more of the same.

Although artificial reality systems are commonly implemented for gaming and other entertainment purposes, such systems are also implemented for purposes outside of recreation. For example, governments may use them for military training simulations, doctors may use them to practice surgery, engineers may use them as visualization aids, and co-workers may use them to facilitate inter-personal interactions and collaboration from across the globe.

Traditional artificial reality systems may incorporate hands-on controllers that enable users to enter input capable of modifying their artificial reality experiences. Unfortunately, these hands-on controllers may limit the users' mobility and/or movements, especially hand-based actions and/or gestures. To resolve these limitations, some artificial reality systems may incorporate traditional wearables capable of sensing a few motions, actions, and/or gestures made by users. The sensing of other motions, actions, and/or gestures, however, has proved challenging and/or impracticable via such traditional wearables.

For example, some traditional wearables may be unable to accurately detect and/or track a finger on a user's right hand touching a certain area on the user's left hand. Additionally or alternatively, some traditional wearables may be unable to identify and/or determine the relative location at which a finger on a user's right hand made contact with the user's left hand. One reason for these deficiencies in such traditional wearables may be the lack of calibration to the user's skin.

Unfortunately, the impedance of people's skin may differ from one person to the next. Even more, the impedance of one person's skin may vary from one area to the next and/or from one time of day to another, depending on a number of different factors (e.g., hydration levels, physiological states, body fat levels, etc.). These variances in impedance of a person's skin may give rise to a need for users to calibrate their wearables on a regular basis (e.g., prior to each use). Without such calibration, the accuracy of these wearables' sensing features may suffer, potentially resulting in false positives and/or false negatives. The instant disclosure, therefore, identifies and addresses a need for additional systems and methods for calibrating wearables based on impedance levels of users' skin surfaces.

As will be described in greater detail below, to calibrate to the current impedance of a user's skin, a wearable may inject a test signal with known parameters (such as known voltage and/or current) to the user's skin from a known point. The wearable may then detect and/or measure the test signal at a particular electrode and then determine the current impedance of the user's skin based at least in part on that measurement of the test signal and the known distance between the injection point and the measuring electrode. Upon determining the current impedance of the user's skin, the wearable may calibrate its sensors and/or processing devices to account for the current impedance of the user's skin by storing the current impedance of the user's skin for use in future calculations related to sensing body contact on the user.

The following will provide, with reference to FIGS. 1-9, detailed descriptions of various systems, components, and/or implementations of wearables capable of self-calibrating based on impedance levels of users' skin surfaces. The discussion corresponding to FIG. 10 will provide detailed descriptions of an exemplary method for calibrating wearables based on impedance levels of users' skin surfaces. The discussion corresponding to FIGS. 11-16 will provide detailed descriptions of types of exemplary artificial reality devices and/or systems that may facilitate and/or contribute to users' artificial reality experiences.

FIG. 1 illustrates an exemplary wearable device 100 that facilitates calibration based on the impedance levels of users' skin surfaces. In some examples, the terms "wearable" and "wearable device" may refer to any type or form of computing device that is worn by a user of an artificial reality system and/or visual display system as part of an article of clothing, an accessory, and/or an implant. Examples of wearable devices include, without limitation, wristbands, pendants, bracelets, rings, jewelry, anklebands, clothing, electronic textiles, shoes, clips, headsets, headbands, head-mounted displays, wristbands, gloves, glasses, variations or combinations of one or more of the same, and/or any other suitable wearable accessories.

As illustrated in FIG. 1, exemplary wearable device 100 may include an electrode 102, a signal generator 104, an electrode 106, a sensor 108, and a processing device 110. In one example, wearable device 100 may be dimensioned to be donned and/or worn by a user of an artificial reality system. For example, the user may fasten wearable device 100 to one of his or her wrists as a wristband.

In some examples, electrodes 102 and 106 may be dimensioned to interface with a skin surface of the user of the artificial reality system. In such examples, electrodes 102 and 106 may be spaced and/or positioned a known distance from one another on wearable device 100. In one example, signal generator 104 may be communicatively coupled to electrode 102, and sensor 108 may be communicatively coupled to electrode 106. Additionally or alternatively, processing device 110 may be communicatively coupled to sensor 108.

Signal generator 104 may include and/or represent an electrical device that generates and/or produces electromagnetic test signals and/or waves. In some examples, signal generator 104 may generate and/or produce a high-frequency electromagnetic signal for injection into the user's skin via electrode 102. The high-frequency electromagnetic signal may oscillate and/or propagate at any suitable frequency. For example, the high-frequency electromagnetic signal may have and/or be characterized by a frequency within the range of 10 kilohertz and 100 megahertz.

Similarly, the high-frequency electromagnetic signal may exhibit and/or maintain any suitable amplitude. For example, the high-frequency electromagnetic signal may have and/or be characterized by an amplitude within the range of 500 millivolts and 5 volts. Additionally or alternatively, the high-frequency electromagnetic signal may include and/or represent any suitable level of electric current. For example, the high-frequency electromagnetic signal may have and/or be characterized by an electric current within the range of 100 microamps and 10 milliamps.

Sensor 108 may include and/or represent an electrical device that detects, senses, and/or measures electromagnetic test signals and/or waves. In some examples, sensor 108 may detect, sense, and/or measure a high-frequency electromagnetic signal generated by signal generator 104 via electrode 106. In such examples, the high-frequency electromagnetic signal may traverse a portion and/or section of the user's skin between electrode 102 and electrode 106. In one example, sensor 108 may measure certain characteristics (such as frequency, amplitude, and/or electric current level) of the high-frequency electromagnetic signal upon its arrival at electrode 106.

Processing device 110 may include and/or represent a hardware-implemented processing device capable of interpreting and/or executing computer-readable instructions. In one example, processing device 110 may obtain electrical signals (whether analog or digital) representative of a high-frequency electromagnetic signal detected, sensed, and/or measured by sensor 108. Additionally or alternatively, processing device 110 may obtain computer-readable data representative of the high-frequency electromagnetic signal detected, sensed, and/or measured by sensor 108. Either way, processing device 110 may analyze certain characteristics (such as frequency, amplitude, and/or electric current level) of the high-frequency electromagnetic signal to determine the current impedance level of the user's skin. Upon determining the current impedance level of the user's skin, processing device 110 may calibrate wearable device 200 to account for the current impedance level of the user's skin.

In addition to the various components illustrated in FIG. 1, exemplary wearable device 100 may include one or more other components that are not illustrated and/or labelled in FIG. 1. For example, wearable device 100 may include and/or incorporate batteries, electronic assemblies, circuitry, passive or active electrical components, communication interfaces or devices, and/or fasteners. An apparatus for calibrating wearables may include and/or represent all or a portion of wearable device 100 in FIG. 1. Accordingly, wearable device 100 in FIG. 1 may, on its own, constitute and/or amount to an apparatus or system for facilitating calibration based on the current impedance of a user's skin. In addition, although exemplary wearable device 100 includes the various components illustrated in FIG. 1, other embodiments of such wearables may omit and/or exclude one or more of those components.

Figure 2:
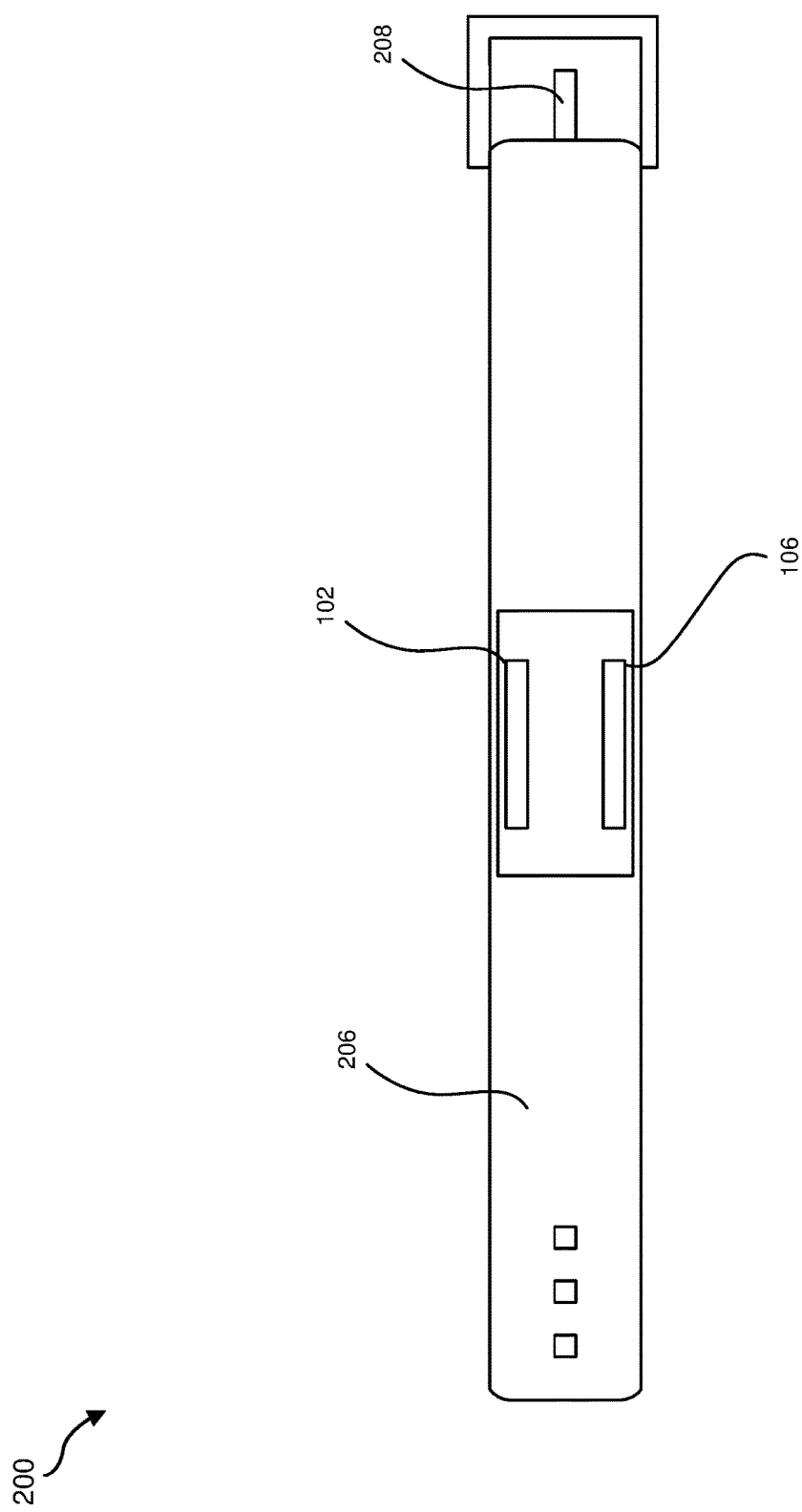
FIG. 2 is an illustration of an exemplary wearable that may be used in connection with embodiments of this disclosure.
Figure 3:
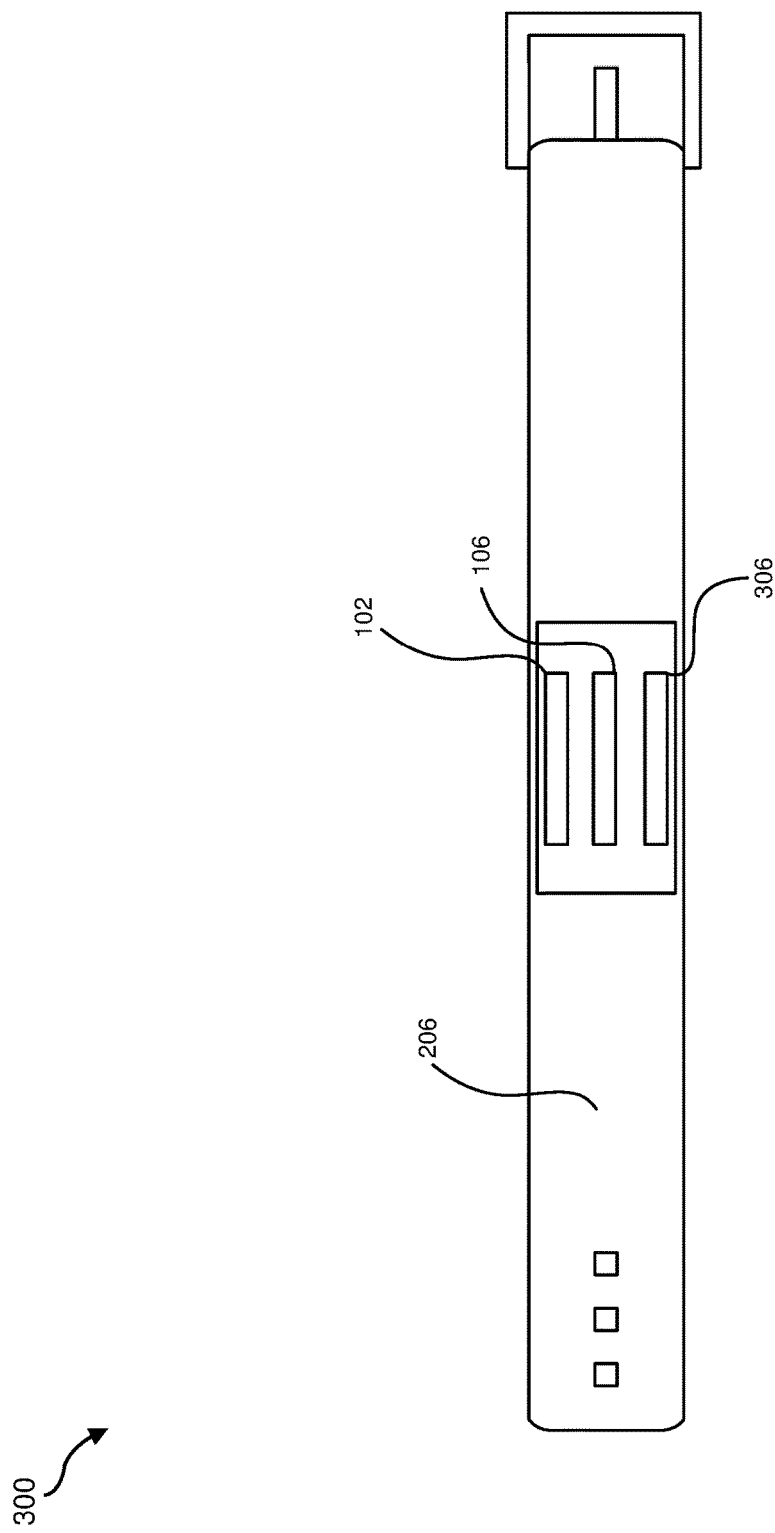
FIG. 3 is an illustration of an additional exemplary wearable that may be used in connection with embodiments of this disclosure.
Figure 4:
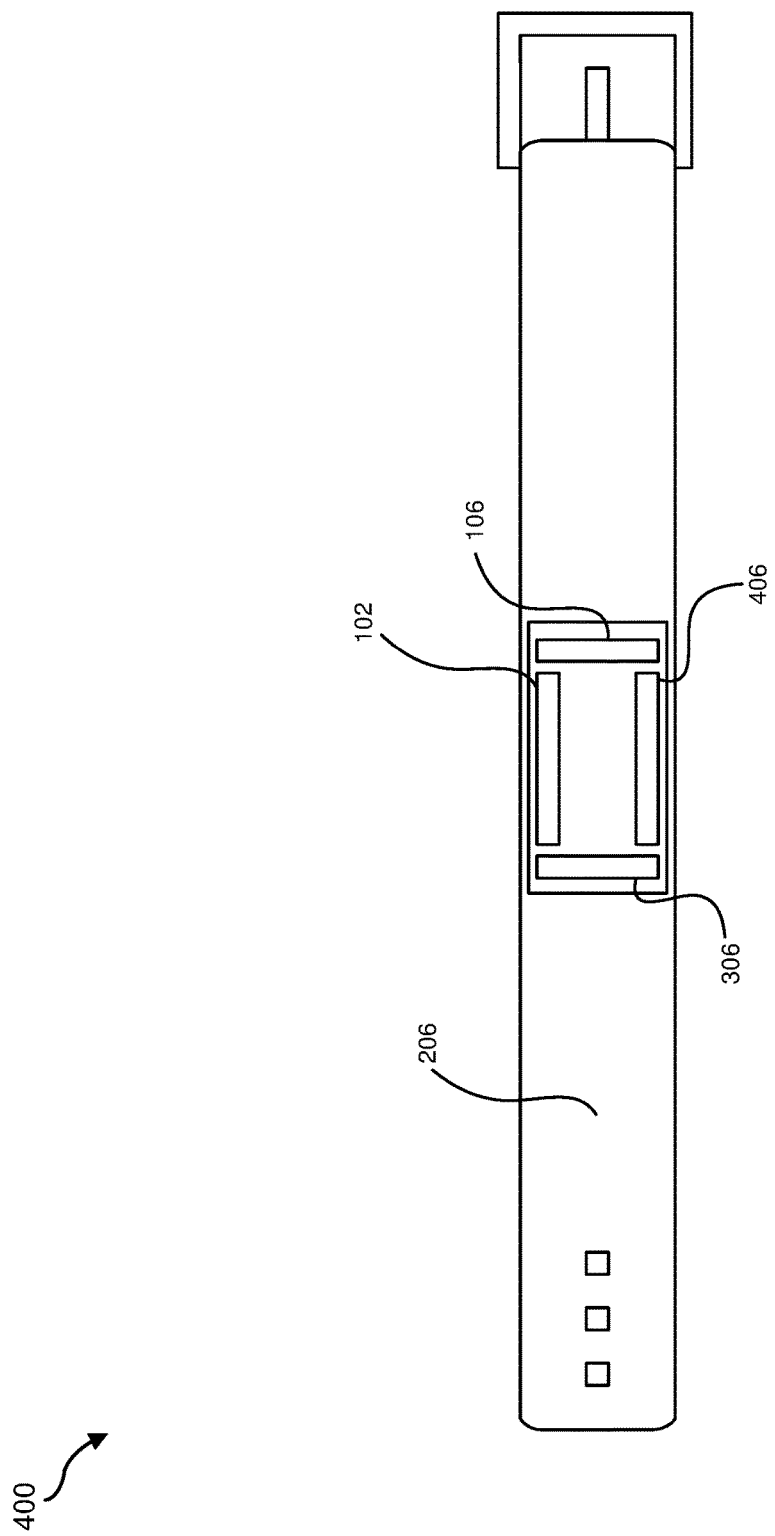
FIG. 4 is an illustration of an additional exemplary wearable that may be used in connection with embodiments of this disclosure.

Exemplary wearable device 100 may be implemented in a variety of ways, including any of those illustrated in FIGS. 2-4. FIG. 2 illustrates an exemplary wearable device 200 that facilitates calibration based on the impedance levels of users' skin surfaces. As illustrated in FIG. 2, wearable device 200 may include and/or represent a wristband 206 and electrodes 102 and 106. In one example, wristband 206 may include and/or incorporate a fastener 208 dimensioned to facilitate securing wearable device 200 to the wrist of a user of an artificial reality system. In this example, when wearable device 200 is coupled and/or secured to the user's wrist via fastener 208, wearable device 200 may be designed and/or dimensioned such that electrodes 102 and 106 interface and/or make physical contact with the user's skin. In this example, electrodes 102 and 106 may be spaced and/or positioned a known distance from one another on wearable device 200.

Wristband 206 may include and/or represent a strap designed and/or dimensioned to at least partially encompass the user's wrist. Wristband 206 may include and/or contain a variety of different materials. Examples of such materials include, without limitation, cottons, polyesters, nylons, elastics, plastics, neoprene, rubbers, metals, combinations or variations of one or more of the same, and/or any other suitable materials. Wristband 206 may be defined and/or formed in a variety of shapes and/or sizes with the aim of securing wearable 200 to the users' wrist. In some examples, wristband 206 may be adjustable to provide a one-size-fits-most feature.

Various configurations and/or designs of wearable devices may be implemented to achieve certain benefits, improvements, and/or goals. Wearable device 200 may include and/or incorporate any suitable number of electrodes to facilitate accurate calibration and/or tracking subsequent body contact or touching. For example, the design of wearable device 200 may include and/or incorporate two electrodes. In this example, the design of wearable device 200 may maximize the distance between electrodes 102 and 106. In other words, wearable device 200 may implement a configuration and/or design in which the spacing between electrodes 102 and 106 is extended to the maximum limit within the physical constraints of wearable device 200. By maximizing the distance between electrodes 102 and 106 in this way, wearable device 200 may be able to improve the accuracy of the impedance measurements and/or test results.

FIG. 3 illustrates an exemplary wearable device 300 that facilitates calibration based on the impedance levels of users' skin surfaces. As illustrated in FIG. 3, wearable device 300 may include and/or represent wristband 206 and electrodes 102, 106, and 306. In one example, when wearable device 300 is coupled and/or secured to a user's wrist, wearable device 300 may be designed and/or dimensioned such that electrodes 102, 106, and 306 interface and/or make physical contact with the user's skin. In this example, electrodes 102, 106, and 306 may be spaced and/or positioned a known distance from one another on wearable device 300.

FIG. 4 illustrates an exemplary wearable device 400 that facilitates calibration based on the impedance levels of users' skin surfaces. As illustrated in FIG. 4, wearable device 400 may include and/or represent wristband 206 and electrodes 102, 106, 306, and 406. In one example, when wearable device 400 is coupled and/or secured to a user's wrist by a fastener, wearable device 400 may be designed and/or dimensioned such that electrodes 102, 106, 306, and 406 interface and/or make physical contact with the user's skin. In this example, electrodes 102, 106, 306, and 406 may be spaced and/or positioned a known distance from one another on wearable device 400.

Figure 5:
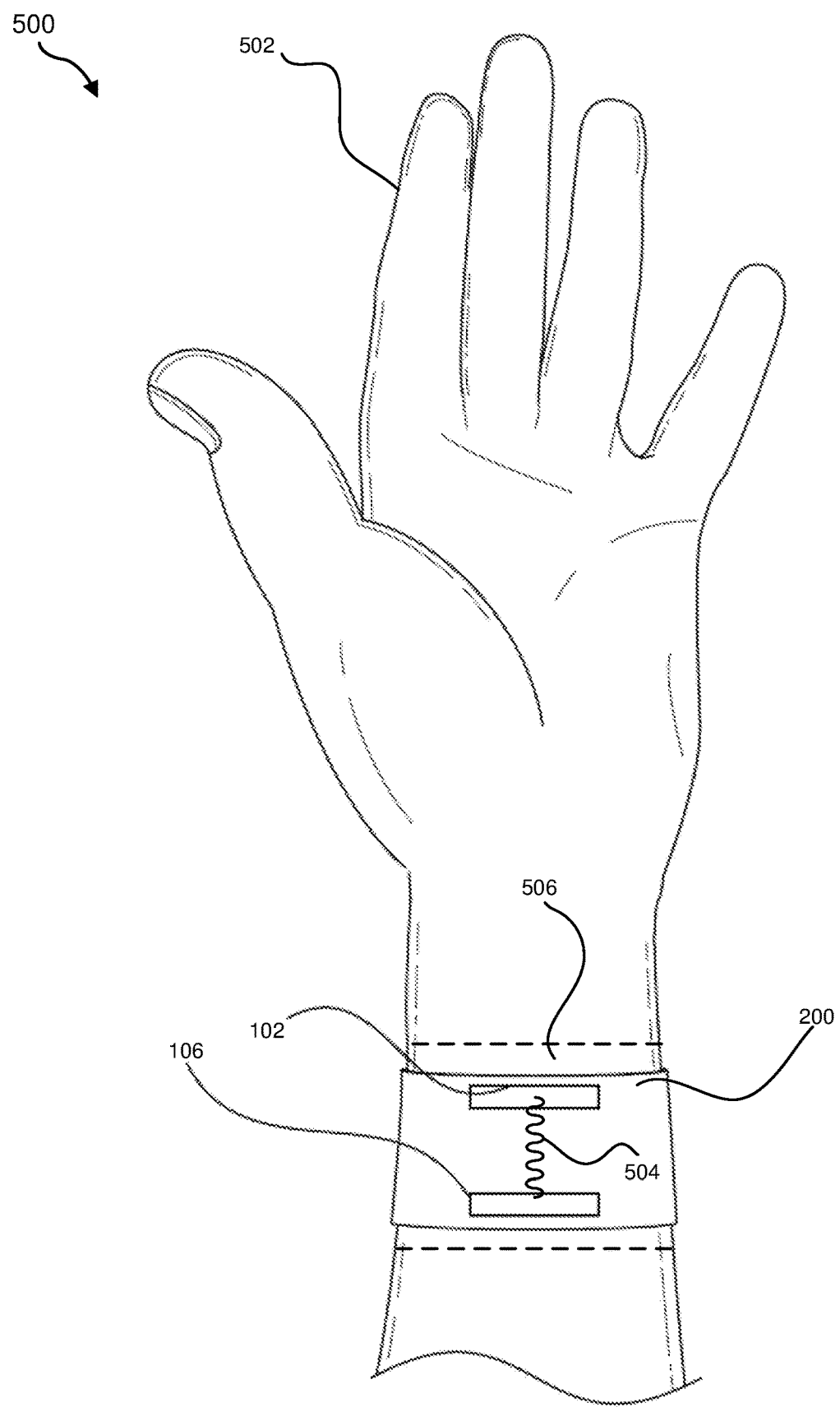
FIG. 5 is an illustration of an exemplary wearable donned on the wrist of a user of an artificial reality system.

FIG. 5 illustrates an exemplary implementation 500 that demonstrates general principles of operation of exemplary wearable device 200 from FIG. 2. As illustrated in FIG. 5, a user 502 may don wearable device 200 on his or her left wrist 506. In one example, wearable device 200 may include and/or incorporate electrodes 102 and 106 spaced and/or positioned a known distance from one another. In this example, signal generator 104 (not illustrated in FIG. 5) may inject a test signal 504 into the user's skin at wrist 506 via electrode 102.

In some examples, signal generator 104 may generate test signal 504 such that test signal 504 is injected into the user's skin with certain known characteristics. For example, at the time of injection into the user's skin, test signal 504 may have a known frequency, a known voltage level or amplitude, and/or a known current level. In one example, test signal 504 may have a frequency within the range of 10 kilohertz and 100 megahertz, an amplitude within the range of 500 millivolts and 5 volts, and/or an electric current within the range of 100 microamps and 10 milliamps.

In some examples, test signal 504 may propagate and/or traverse the user's skin at wrist 506 from electrode 102 to electrode 106. The user's body may serve as the medium through which test signal 504 propagates and/or traverses from electrode 102 to electrode 106. In one example, the user's body may include organic matter capable of carrying test signal 504 across the user's skin at wrist 506. For example, the user's skin at wrist 506 may facilitate the test signal's propagation and/or traversal. In this example, the user's skin at wrist 506 may naturally exhibit and/or produce a certain impedance.

In some examples, test signal 504 may arrive at electrode 106 via the user's skin at wrist 506. In such examples, electrode 106 on wearable device 200 may receive test signal 504 and pass the same to sensor 108. In one example, sensor 108 on wearable device 200 may measure test signal 504 as received by electrode 106. In this example, processing device 110 on wearable device 200 may then determine and/or estimate a current impedance of the user's skin at wrist 506. This determination may be based at least in part on the known distance between electrodes 102 and 106 on wearable device 200 and the measurement of test signal 504 as received by electrode 106.

In some examples, the measurement of test signal 504 may involve identifying certain characteristics of test signal 504 as received by electrode 106. For example, processing device 110 may identify one or more characteristics of test signal 504 as received by electrode 106. In this example, the current impedance of the user's skin at wrist 506 may affect, alter, and/or impair such characteristics of test signal 504. The differential and/or delta of such characteristics from the origin at electrode 102 to the destination at electrode 106 may indicate and/or be used to determine or estimate the current impedance of the user's skin at wrist 506. Examples of such characteristics of test signal 504 include, without limitation, the strength of test signal 504 received by electrode 106, the envelope of test signal 504 received by electrode 106, the frequency of test signal 504 received by electrode 106, the amplitude of test signal 504 received by electrode 106, combinations or variations of one or more of the same, and/or any other suitable characteristics.

In some examples, the user's skin may have a certain impedance per unit of distance and/or area. The user's skin may also have a certain linear and/or nonlinear frequency response. Accordingly, the user's skin may also exhibit different impedances depending on the frequency of the test signal. For example, the user's skin may exhibit an impedance of 500 kiloohms per centimeter in response to a 1-hertz test signal. However, the same user's skin may exhibit an impedance of 300 ohms per centimeter in response to a 1-megahertz test signal.

As a specific example, electrodes 102 and 106 on wearable device 200 may be spaced 3 centimeters apart. In this example, electrode 102 may emit a 1-milliamp test signal with an amplitude of 1.5 volts and a frequency of 10 megahertz, and electrode 106 may detect and/or receive the test signal via an impedance divider circuit 600 in FIG. 6.

The impedance of the user's skin between electrodes 102 and 106 may alter certain characteristics of the test signal. For example, the test signal may arrive at electrode 106 with an amplitude of 0.6 volts, as opposed to 1.5 volts.

Figure 6:
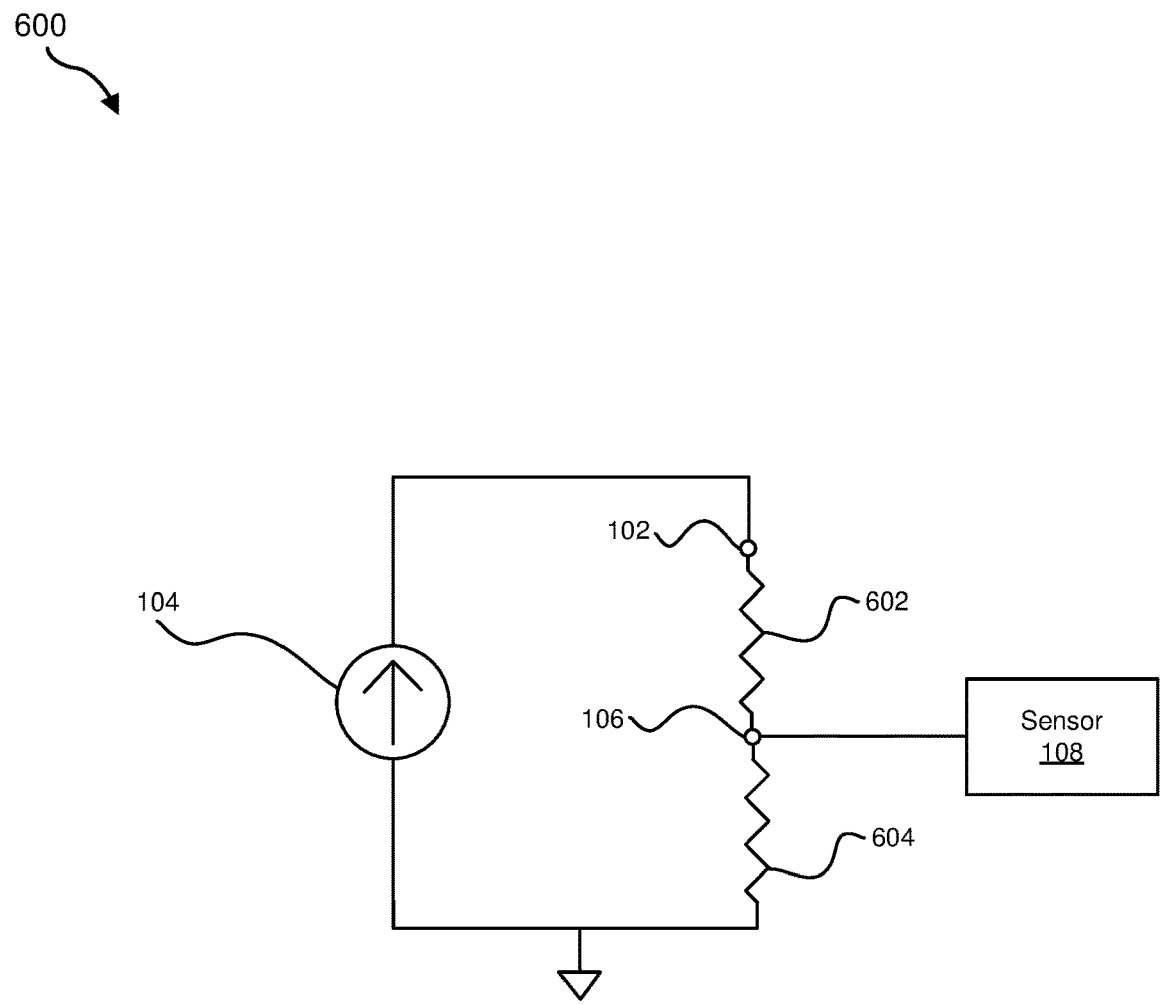
FIG. 6 is an illustration of an exemplary impedance divider circuit incorporated at least in part into a wearable donned by a user of an artificial reality system.

As illustrated in FIG. 6, impedance divider circuit 600 may include signal generator 104, electrodes 102 and 106, impedance components 602 and 604, and sensor 108. In some examples, one part of impedance divider circuit 600 may be incorporated into wearable device 200, and another part of impedance divider circuit 600 may be the user's skin at wrist 506. For example, impedance component 602 may represent the user's skin at wrist 506 that is undergoing impedance testing. Accordingly, impedance component 602 may initially have an impedance level that is unknown. In this example, impedance component 604 may include and/or represent a resistor of known resistance incorporated into the circuitry of wearable device 200. In impedance divider circuit 600, impedance components 602 and 604 may be in series with one another.

Continuing with the above example, processing device 110 may calculate and/or solve for the impedance of the user's skin (e.g., impedance component 602 in FIG. 6) between electrodes 102 and 106 based at least in part on the test signal measurement and various known parameters. For example, impedance divider circuit 600 may include the unknown impedance of the user's skin in series with a 100-ohm resistor. In this example, the 100-ohm resistor may thus form part of impedance divider circuit 600. In the event that the amplitude of the test signal is measured at 0.6 volts at electrode 106, the unknown impedance of the skin may be measured as 50 ohms per centimeter in response to the 10-megahertz test signal $$\left( Z_{skin} = \frac{100 \text{ ohms} \times 1.5 \text{ volts}}{0.6 \text{ volts}} - 100 \text{ ohms} = \right.$$

$$\left. 150 \text{ ohms across 3 centimeters of skin} = 50 \text{ ohms per centimeter} \right).$$

Additionally or alternatively, the test signal may include and/or represent a constant current signal. In this example, the impedance of the skin may be measured without the use of an impedance divider circuit.

In some examples, wearable device 200 may test the impedance of the user's skin with varying frequencies (as in, e.g., a frequency sweep). By using and/or analyzing varying frequencies in this way, wearable device 200 may be able to achieve a more accurate estimation of the current impedance of the user's skin. For example, sensor 108 may measure the test signals of varying frequencies as received by electrode 106. In this example, processing device 110 may analyze a frequency response of the user's skin based at least in part on the measurements of those test signals as received by electrode 106. Processing device 110 may then estimate the current impedance of the user's skin based at least in part on the frequency response of the user's skin.

In one example, wearable device 200 may include and/or implement a model (such as a machine learning model) that represents the relationship and/or correlation between the impedance at the user's wrist between electrodes 102 and 106 and the impedance between the user's hand (e.g., at the palm area) and the user's wrist. For example, wearable device 200 may include and/or implement a model that assumes the impedance at the user's hand is one and a half times the amount of the impedance at the user's wrist. In another example, wearable device 200 may include and/or implement a model that assumes the impedance at the user's hand is twice the amount of the impedance at the user's wrist. Additionally or alternatively, wearable device 200 may operate on the assumption that the impedance at the user's wrist is the same as the impedance between the user's hand (e.g., at the palm area) and the user's wrist. Further, wearable device 200 may include and/or implement a model that applies a non-linear impedance gradient and/or function between the user's hand and wrist. Upon calculating the current impedance of the user's skin, processing device 110 and/or wearable device 200 may self-calibrate by applying the measured impedance(s) to the model to facilitate sensing and/or tracking contact made on the user's left hand with the user's right hand (or vice versa).

Figure 7:
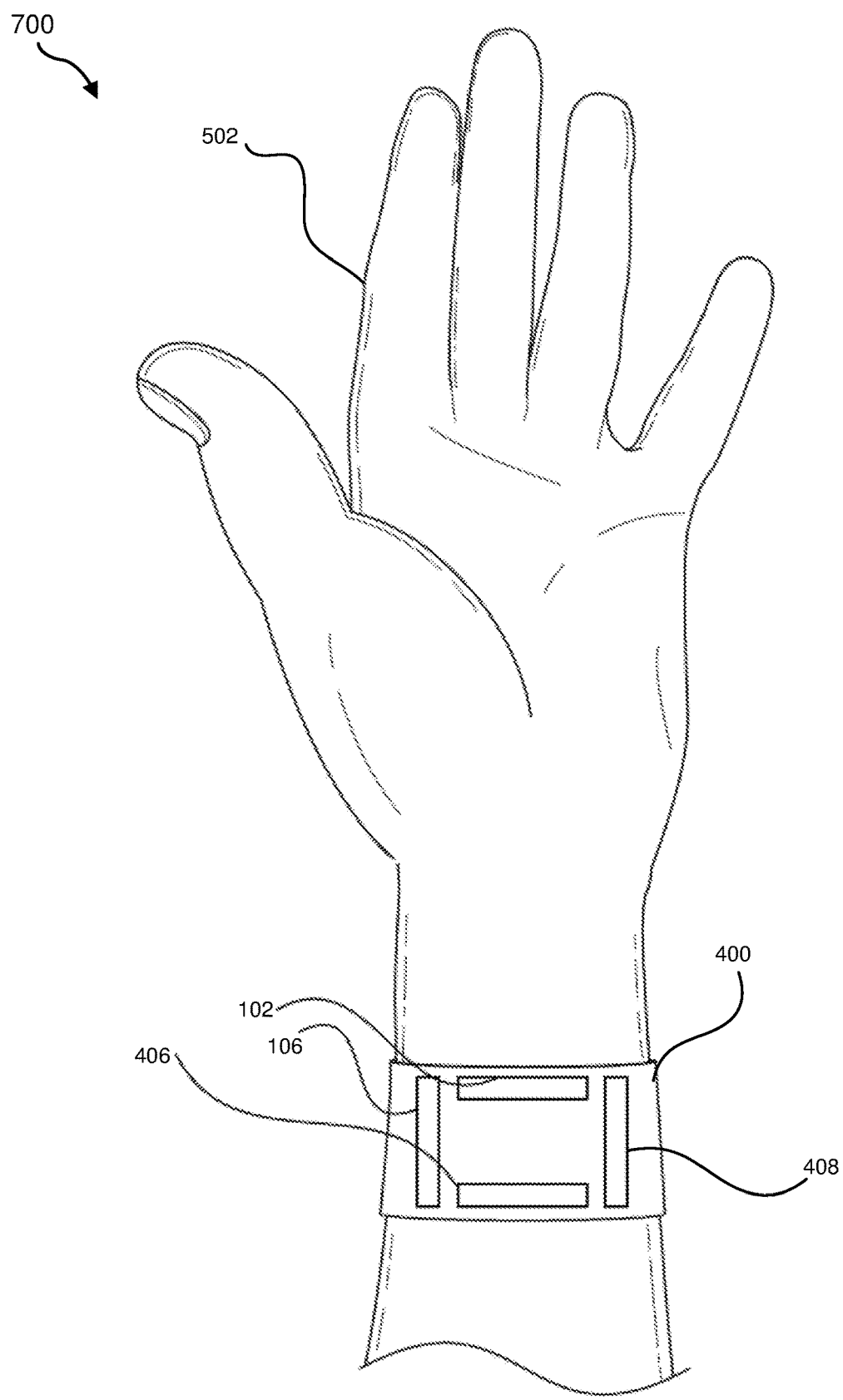
FIG. 7 is an illustration of an additional exemplary wearable donned on the wrist of a user of an artificial reality system.

FIG. 7 illustrates an exemplary implementation 700 that demonstrates general principles of operation of exemplary wearable device 400 from FIG. 4. As illustrated in FIG. 7, a user 502 may don wearable device 400 on his or her left wrist. In some examples, wearable device 400 may include and/or incorporate electrodes 102, 106, 406, and 408. In these examples, electrodes 102, 106, 406, and 408 may be spaced and/or positioned a known distance from one another. In one example, signal generator 104 (not illustrated in FIG. 7) may inject a test signal into the user's skin at his or her wrist via electrode 102.

In some examples, the test signal may propagate and/or traverse the user's skin at his or her wrist from electrode 102 to electrode 106, 406, and/or 408. In these examples, the test signal may arrive at electrode 106, 406, and/or 408 via the user's skin at his or her wrist. In such examples, electrode 106, 406, and/or 408 on wearable device 400 may receive the test signal and pass the same to sensor 108. In one example, sensor 108 on wearable device 400 may measure test signal 504 as received by electrode 106. In this example, processing device 110 on wearable device 400 may then determine a current impedance of the user's skin at his or her wrist. This determination may be based at least in part on the known distance between electrodes 102, 106, 406, and 408 on wearable device 400 and the measurement of the test signal as received by electrode 106, 406, and 408.

Upon calculating the current impedance of the user's skin, processing device 110 may calibrate wearable device 400 by storing the current impedance of the user's skin for use in future calculations related to sensing body contact on the user. Accordingly, processing device 110 and/or wearable device 400 may automatically self-calibrate to account for the current impedance of the user's skin at the beginning of a session during which the user operates wearable device 400.

Figure 8:
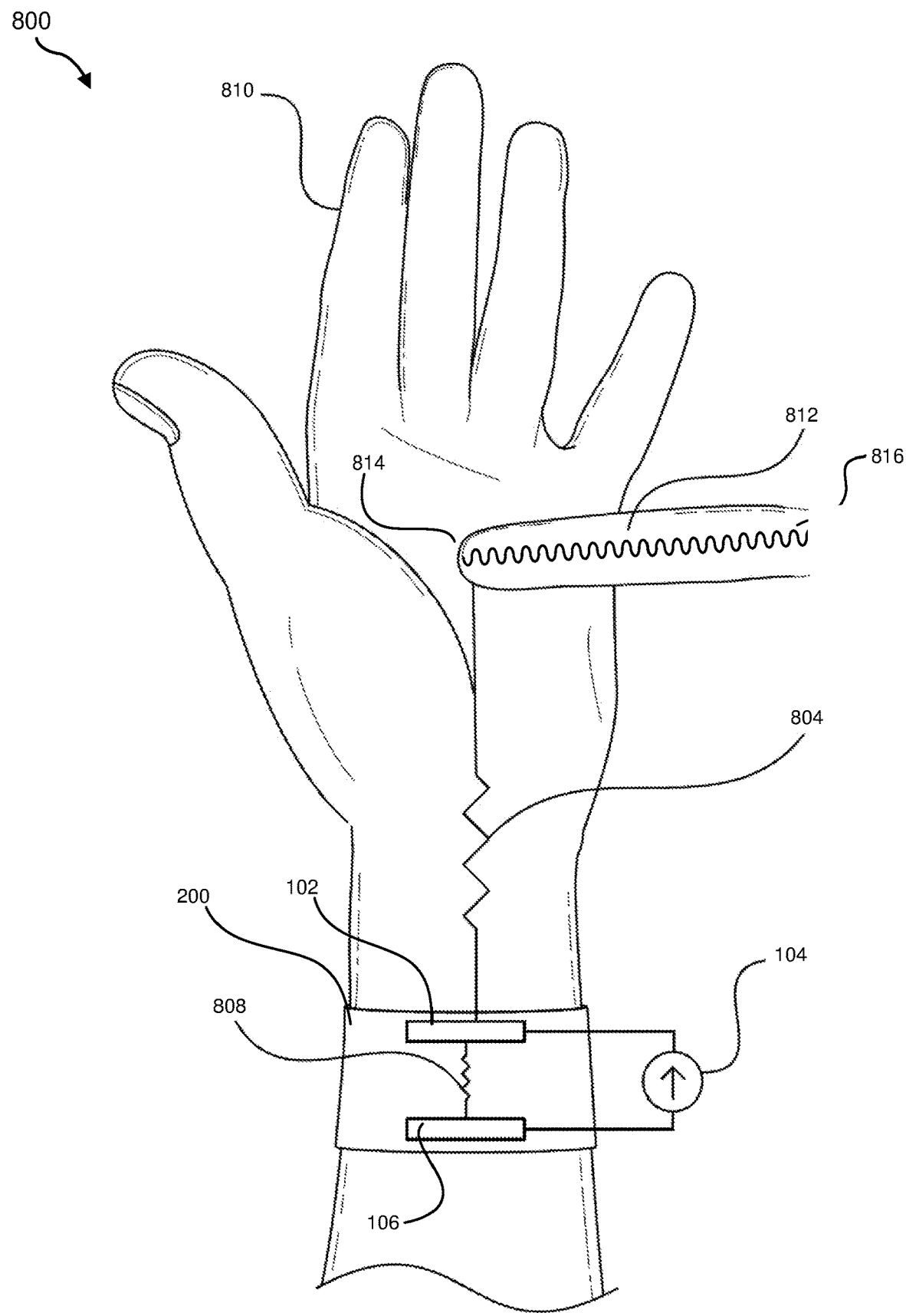
FIG. 8 is an illustration of an exemplary implementation in which a user dons a wearable proximate to one hand and touches that hand with a finger on the user's other hand.

FIG. 8 illustrates an exemplary implementation 800 in which a user donning exemplary wearable device 200 from FIG. 2 touches a certain point on his or her left hand with his or her right hand. As illustrated in FIG. 8, a user may don wearable device 200 on his or her left wrist. In some examples, wearable device 200 may determine a current impedance 808 of the skin surface at the user's wrist by injecting a test signal via signal generator 104. In these examples, wearable device 200 may automatically self-calibrate to account for current impedance 808 at the beginning of an operating session.

In some examples, processing device 110 on wearable device 200 may implement and/or apply a model (such as a machine learning model) that represents the relationship between the impedance levels at the user's wrist and at the user's hand. By implementing and/or applying the model in this way, processing device 110 on wearable device 200 may be able to estimate and/or approximate a current impedance 804 of the skin surface between the user's wrist and the user's hand. In one example, such a model may be developed with data collected via a large-scale study of human hands and/or one-time calibration of each user (e.g., data collected from a user touching 9 points on a 3×3 grid projected onto his or her palm).

In one example, the user may also don an additional wearable (not illustrated in FIG. 8) on his or her right wrist. In this example, the additional wearable donned on the user's right wrist may transmit and/or emit a Radio Frequency (RF) signal 816. In some embodiments, the frequency of RF signal 816 may match and/or correspond to the frequency of test signal 504 used to calculate the current impedance of the user's skin. For example, both RF signal 816 and test signal 504 may have a frequency of 10 megahertz.

When the user touches his or her left hand 810 with a finger on his or her right hand 812, that finger may serve as a bridge that carries RF signal 816 from right hand 812 to a touch point 814 on left hand 810. From touch point 814, RF signal 816 may traverse through the user's skin toward wearable device 200 at the user's left wrist. As RF signal 816 arrives at the user's left wrist, wearable device 200 at the user's left wrist may detect and/or sense RF signal 816. For example, electrodes 102 and 106 on wearable device 200 may receive RF signal 816 as it reaches the user's wrist after traversing the user's skin down from touch point 814.

In some examples, wearable device 200 may analyze RF signal 816 to identify and/or measure certain characteristics and/or parameters of RF signal 816. For example, sensor 108 and/or another sensor may be communicatively coupled to electrode 102, and sensor 108 and/or the other sensor may measure the signal strength of RF signal 816 as received by electrodes 102 and 106, respectively. Examples of such characteristics and/or parameters include, without limitation, the power or strength of the RF signal, the envelope of the RF signal, the amplitude (such as the root mean square amplitude) or amplitude ratio of the RF signal, a differential of the RF signal as detected by the different electrodes, combinations or variations of one or more of the same, and/or any other suitable characteristics and/or parameters.

In some examples, processing device 110 and/or wearable device 200 may use one or more of these characteristics and/or parameters of RF signal 816 to determine that the user's finger on right hand 812 has made physical contact with left hand 810. For example, wearable device 200 may monitor for a 10-megahertz RF signal at electrodes 102 and 106. In this example, wearable device 200 may detect and/or receive RF signal 816 via both of electrodes 102 and 106. Upon detecting and/or receiving RF signal 816, wearable device 200 may determine that the user has touched left hand 810 with a finger on right hand 812.

Additionally or alternatively, processing device 110 on wearable device 200 may use one or more of these characteristics and/or parameters of RF signal 816 to identify and/or determine touch point 814. In one example, touch point 814 may represent the relative location at which the finger from right hand 812 made contact with left hand 810. For example, processing device 110 may examine the strength of RF signal 816 as detected by both of electrodes 102 and 106. Accordingly, the strength of RF signal 816 as received by electrode 102 may differ from the strength of RF signal 816 as received by electrode 106. In other words, the signal strength of RF signal 816 may be perceived differently by electrodes 102 and 106 relative to one another. In this example, processing device 110 may determine the location of touch point 814 relative to wearable device 200 based at least in part on the current impedance of the user's skin and the signal strength of RF signal 816 as received by electrodes 102 and 106.

In some examples, the additional wearable donned on the user's right wrist may transmit and/or emit RF signals of multiple frequencies. When the user touches left hand 810 with a finger on right hand 812, that finger may serve as a bridge that carries the RF signals of multiple frequencies from right hand 812 to touch point 814 on left hand 810. From touch point 814, the RF signals of multiple frequencies may traverse through the user's skin toward wearable device 200. As the RF signals of multiple frequencies arrive at the user's left wrist, the wearable device 200 may detect and/or sense the RF signals of multiple frequencies. By using and/or analyzing RF signals of multiple frequencies in this way, wearable device 200 may be able to achieve a more accurate estimation of the relative location of touch point 814 on left hand 810.

In some examples, wearable device 200 and the additional wearable may be incorporated into and/or represent part of an artificial reality system (such as any of those illustrated in FIGS. 11-16). Touch events performed by the user (e.g., at touch points on left hand 810) may correspond to and/or represent input for the artificial reality system. In one example, the artificial reality system may modify at least one virtual component of the user's artificial reality experience to account for the touch events performed by the user. Additionally or alternatively, processing device 110 on wearable device 200 may facilitate modifying at least one virtual component of the artificial reality system to account for a touch event based on touch point 814. For example, processing device 110 may generate one or more input commands for the artificial reality system that account for the touch event based on touch point 814. Those input commands may modify the visual display presented by the artificial reality system to the user as part of his or her artificial reality experience.

In some examples, wearable device 200 may serve as a receiver, and the additional wearable may serve as a transmitter. However, different and/or opposite configurations may also be possible and/or workable (e.g., the right-side wearable serving as the receiver and the left-side wearable serving as the transmitter). Accordingly, users may be able to customize the configuration of right-side and left-side wearables based on whether they are right-handed or left-handed. Additionally or alternatively, the roles of the users' right and left hands may be dynamically reconfigured and/or reversed with respect to the wearable devices. As a result, the wearable devices may be able to collect and/or obtain additional asymmetrical data and/or information for use in pinpointing the exact location of the users' fingers and/or touch points.

Figure 9:
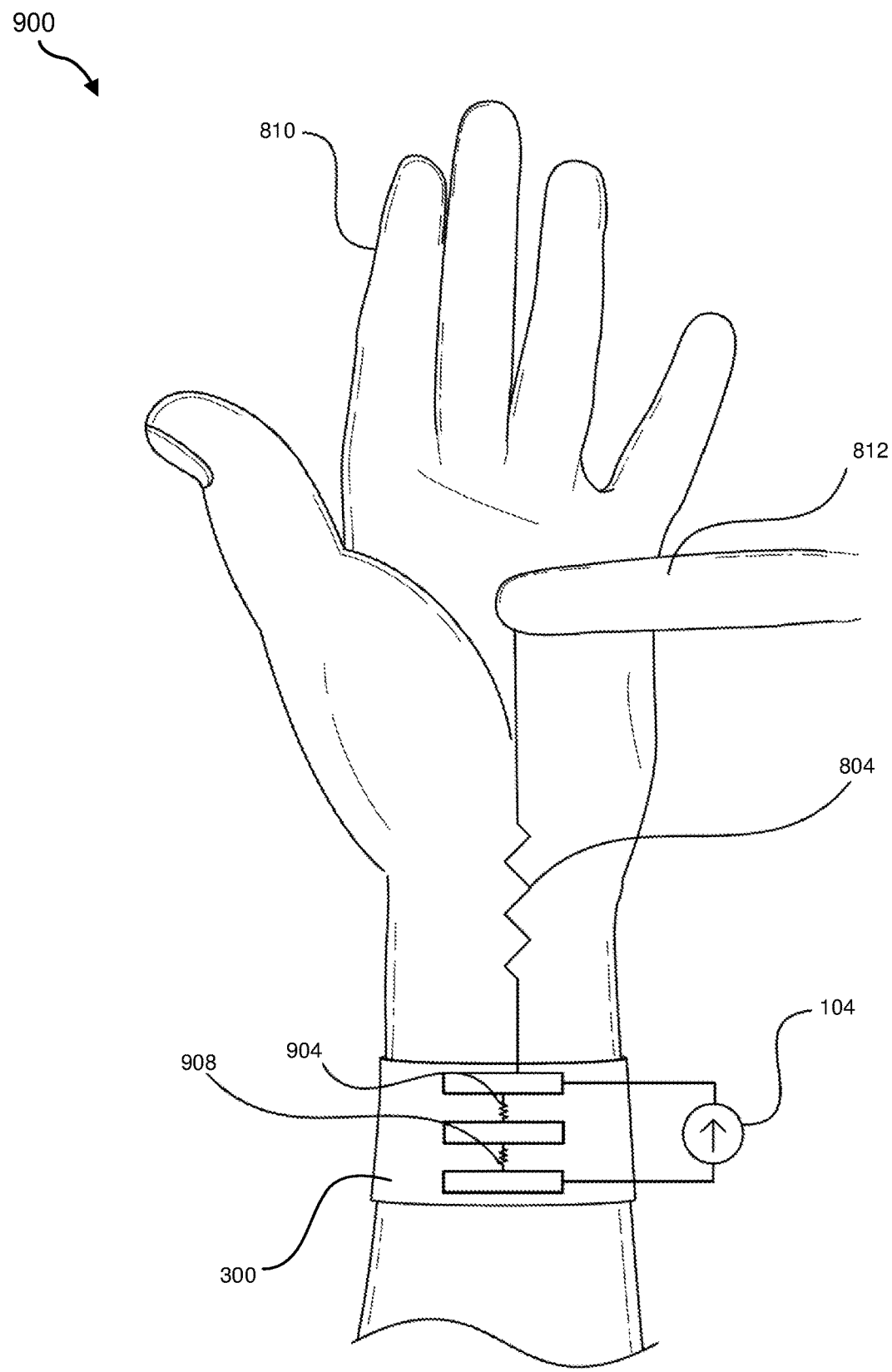
FIG. 9 is an illustration of an exemplary implementation in which a user dons a wearable proximate to one hand and touches that hand with a finger on the user's other hand.

FIG. 9 illustrates an exemplary implementation 900 in which a user donning exemplary wearable device 300 from FIG. 3 touches a certain point on his or her left hand with his or her right hand. As illustrated in FIG. 9, a user may don wearable device 300 on his or her left wrist. In some examples, wearable device 300 may determine a current impedance 904 of the skin surface between electrodes 102 and 106 at the user's wrist and/or a current impedance 908 of the skin surface between electrodes 106 and 306 at the user's wrist. In these examples, wearable device 300 may automatically self-calibrate to account for current impedances 904 and 908 at the beginning of an operating session.

In one example, electrodes 102, 106, and 306 on wearable device 300 may be spaced and/or separated from one another by a certain distance in the x-direction and/or along the x-axis relative to left hand 810. In this example, sensor 108 on wearable device 300 may take measurements of RF signal 816 transmitted from the additional wearable as detected via electrodes 102, 106, and 306 spaced in the x-direction and/or along the x-axis. Processing device 110 on wearable device 300 may then calculate the distance between touch point 814 on left hand 810 and electrodes 102, 106, and 306 at the user's left wrist. In some embodiments, electrodes 102, 106, and 306 may facilitate measuring and/or estimating the distance from wearable device 300 to touch point 814 in the x-direction and/or along the x-axis.

Additionally or alternatively, electrodes 102, 106, and 306 on wearable device 300 may be spaced and/or separated from one another by a certain distance in the y-direction and/or along the y-axis relative to left hand 810. In this example, sensor 108 on wearable device 300 may take measurements of RF signal 816 transmitted from the additional wearable as detected via electrodes 102, 106, and 306 spaced in the y-direction and/or along the y-axis. Processing device 110 on wearable device 300 may then calculate the distance between touch point 814 on left hand 810 and electrodes 102, 106, and 306 at the user's left wrist. In some embodiments, electrodes 102, 106, and 306 may facilitate measuring and/or estimating the distance from wearable device 300 to touch point 814 in the y-direction and/or along the y-axis.

In some examples, wearable device 300 may use and/or combine such measurements from the various electrodes to determine and/or estimate the relative position of touch point 814 on left hand 810. In other words, wearable device 300 may be able to map the finger from right hand 812 to touch point 814 on left hand 810 by way of triangulation. This calculation may be performed in a variety of different ways. For example, wearable device 300 may perform a differential operation on RF signal 816 relative to the readings taken from the multiple electrodes. By repeatedly taking such measurements and performing these calculations, wearable device 300 may be able to effectively track the finger from right hand 812 as it moves across left hand 810.

In some examples, wearable device 300 may be able to detect and/or identify certain gestures and/or input commands made by the user. For example, wearable device 300 may be able to determine that the user made a swiping motion and/or gesture across left hand 810. In this example, wearable device 300 may be able to identify the direction of the swiping motion and/or gesture (along, e.g., the x-axis and/or the y-axis) by whether the strength of RF signal 816 increases or decreases with respect to electrodes 102, 106, and 306.

Figure 10:
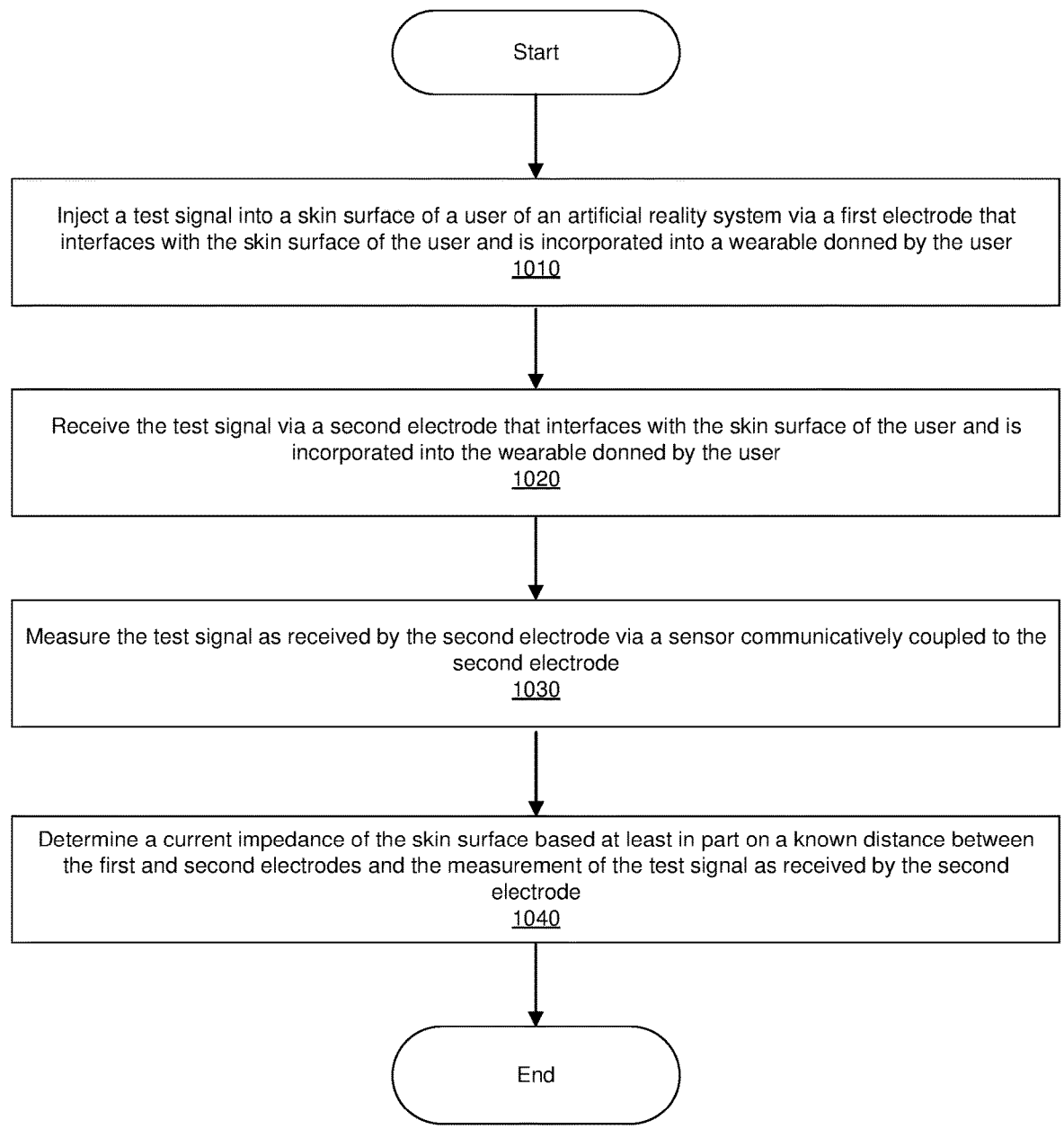
FIG. 10 is a flowchart of an exemplary method for calibrating wearables based on impedance levels of users' skin surfaces.

FIG. 10 is a flow diagram of an exemplary method 1000 for calibrating wearables based on impedance levels of users' skin surfaces. The steps shown in FIG. 10 may be performed by certain devices incorporated into a wearable of an artificial reality system. Additionally or alternatively, one or more of the steps shown in FIG. 10 may be performed by a remote computing device (such as a nearby laptop) that receives certain data from a wearable (via, e.g., wireless transmission). Moreover, the steps shown in FIG. 10 may also incorporate and/or involve various sub-steps and/or variations consistent with the descriptions provided above in connection with FIGS. 1-9.

As illustrated in FIG. 10, at step 1010, a wearable device donned by a user of an artificial reality system may inject a test signal into a skin surface of the user via a first electrode that interfaces with the skin surface of the user. For example, signal generator 104 on wearable device 100 may inject test signal 504 into the skin at user's wrist 506 via electrode 102. At the time of injection, test signal 504 may have certain known parameters, such as frequency, amplitude, and/or current level.

At step 1020 in FIG. 10, the wearable device may receive the test signal via a second electrode that interfaces with the skin surface of the user. For example, test signal 504 may traverse the user's skin from electrode 102 to electrode 106. In this example, electrode 106 may receive test signal 504 as it arrives via the user's skin. At the time of receipt, test signal 504 may have certain measurable parameters, such as frequency, amplitude, and/or current level.

At step 1030 in FIG. 10, the wearable device may measure the test signal as received by the second electrode via a sensor communicatively coupled to the second electrode. For example, sensor 108 on wearable device 100 may receive test signal 504 from electrode 106. In this example, sensor 108 may measure the strength of test signal 504 as received via electrode 106. The strength of test signal 504 may include and/or involve the amplitude and/or current level.

At step 1040 in FIG. 10, the wearable device may determine the current impedance of the skin surface based at least in part on the known distance between the first and second electrodes and the measurement of the test signal as received by the second electrode. For example, processing device 110 on wearable device 100 may calculate current impedance 808 of the skin surface at the user's wrist. In this example, the calculation may rely on the known distance between electrodes 102 and 106 on wearable device 200, the known parameters of test signal 504 at the time of injection, and the measured parameters of test signal 504 at the time of receipt.

As described above in connection with FIGS. 1-10, a wearable donned by a user of an artificial reality system may automatically self-calibrate to account for the current impedance of the user's skin at the beginning of each operating session. For example, a wearable at the user's left wrist may serve as a receiver while a wearable at the user's right wrist serves as a transmitter. The wearable at the user's left wrist may include two or more electrodes spaced a known distance from one another. To calibrate the wearable at the user's left wrist to serve as the receiver, this wearable may inject a test signal with known parameters (such as voltage and/or current) into the user's skin from one of the electrodes. Once injected, the test signal may traverse through the user's skin toward one of the electrodes included on the wearable at the user's left wrist. As the test signal arrives at that electrode, the wearable at the user's left wrist may detect and/or sense the test signal.

In some examples, the wearable at the user's left wrist may analyze the received test signal to identify and/or measure certain characteristics and/or parameters. In such examples, the wearable may use one or more of these characteristics and/or parameters of the received test signal to determine the impedance of the user's skin per unit of distance between the electrodes at that point in time. The determined impedance of the user's skin may also enable the wearable at the user's left wrist to estimate the distance and/or location of a touch point made on the user's left hand with a finger from the user's right hand.

EXAMPLE EMBODIMENTS

Example 1: A wearable may include (1) a plurality of electrodes dimensioned to interface with a skin surface of a user of an artificial reality system, wherein the electrodes are spaced a known distance from one another, (2) a signal generator communicatively coupled to one of the electrodes, wherein the signal generator injects a test signal into the skin surface of the user via the one of the electrodes, (3) at least one sensor communicatively coupled to another one of the electrodes, wherein the sensor measures the test signal as received by the another one of the electrodes, and (4) at least one processing device communicatively coupled to the sensor, wherein the processing device determines a current impedance of the skin surface based at least in part on the known distance between the electrodes and the measurement of the test signal as received by the another one of the electrodes.

Example 2: The wearable of Example 1, wherein the test signal injected into the skin surface of the user has a known frequency, a known voltage level, and/or a known current level.

Example 3: The wearable of Example 1, wherein the test signal injected into the skin surface of the user has a frequency within a range of 10 kilohertz and 100 megahertz, an amplitude within a range of 500 millivolts and 5 volts, and/or an electric current within a range of 100 microamps and 10 milliamps.

Example 4: The wearable of Example 1, wherein the processing device identifies one or more characteristics of the measurement of the test signal as received by the another one of the electrodes and then determines, based at least in part on the characteristics of the measurement of the test signal, the current impedance of the skin surface.

Example 5: The wearable of Example 1, wherein the characteristics of the measurement of the test signal comprise a strength of the test signal as received by the another one of the electrodes, an envelope of the test signal as received by the another one of the electrodes, and/or an amplitude of the test signal as received by the another one of the electrodes.

Example 6: The wearable of Example 1, wherein the processing device calibrates the wearable based at least in part on the current impedance of the skin surface by storing the current impedance of the skin surface for use in future calculations related to sensing body contact on the user.

Example 7: The wearable of Example 6, wherein the processing device automatically self-calibrates at a beginning of a session during which the user operates the wearable.

Example 8: The wearable of Example 1, further comprising a resistor of known resistance that forms part of an impedance divider circuit, wherein the impedance divider circuit includes the current impedance of the skin surface in series with the resistor of known resistance.

Example 9: The wearable of Example 1, wherein the signal generator injects a plurality of test signals into the skin surface of the user via the one of the electrodes, the plurality of test signals having varying frequencies, and wherein the sensor measures the plurality of test signals as received by the another one of the electrodes, and wherein the processing device analyzes a frequency response of the skin surface based at least in part on the measurements of the test signals as received by the another one of the electrodes and then estimates the current impedance of the skin surface based at least in part on the frequency response of the skin surface.

Example 10: The wearable of Example 1, further comprising a fastener dimensioned to facilitate securing the wearable to a wrist of the user of the artificial reality system, and wherein the skin surface comprises a wrist area of the user, and wherein the processing device implements a model that represents a relationship between the wrist area of the user and a hand of the user and then estimates a current impedance of an additional skin surface between the wrist area of the user and the hand of the user.

Example 11: The wearable of Example 1, further comprising a fastener that secures the wearable proximate to a first hand of the user of the artificial reality system, and wherein the electrodes receive a radio frequency signal emitted by a transmitter incorporated in an additional wearable secured proximate to a second hand of the user as the second hand makes physical contact with the first hand, and wherein the sensor is communicatively coupled to the electrodes and measures a signal strength of the radio frequency signal as received by the electrodes, and wherein the processing device determines a touch point that represents a relative location at which the second hand makes physical contact with the first hand based at least in part on the current impedance of the skin surface and the signal strength of the radio frequency signal as received by the electrodes.

Example 12: The wearable of Example 11, wherein the processing device facilitates modifying at least one virtual component of the artificial reality system to account for the touch point.

Example 13: A system comprising (1) a plurality of electrodes dimensioned to interface with a skin surface of a user of an artificial reality system, wherein the electrodes are spaced a known distance from one another, (2) a signal generator communicatively coupled to one of the electrodes, wherein the signal generator injects a test signal into the skin surface of the user via the one of the electrodes, (3) at least one sensor communicatively coupled to another one of the electrodes, wherein the sensor measures the test signal as received by the another one of the electrodes, and (4) at least one processing device communicatively coupled to the sensor, wherein the processing device determines a current impedance of the skin surface based at least in part on the known distance between the electrodes and the measurement of the test signal as received by the another one of the electrodes.

Example 14: The system of Example 13, wherein the test signal injected into the skin surface of the user has a known frequency, a known voltage level, and/or a known current level.

Example 15: The system of Example 13, wherein the test signal injected into the skin surface of the user has a frequency within a range of 10 kilohertz and 100 megahertz, an amplitude within a range of 500 millivolts and 5 volts, and/or an electric current within a range of 100 microamps and 10 milliamps.

Example 16: The system of Example 13, wherein the processing device identifies one or more characteristics of the measurement of the test signal as received by the another one of the electrodes and then determines, based at least in part on the characteristics of the measurement of the test signal, the current impedance of the skin surface.

Example 17: The system of Example 13, wherein the characteristics of the measurement of the test signal comprise a strength of the test signal as received by the another one of the electrodes, an envelope of the test signal as received by the another one of the electrodes, and/or an amplitude of the test signal as received by the another one of the electrodes.

Example 18: The system of Example 13, wherein the processing device calibrates the wearable based at least in part on the current impedance of the skin surface by storing the current impedance of the skin surface for use in future calculations related to sensing body contact on the user.

Example 19: The system of Example 18, wherein the processing device automatically self-calibrates at a beginning of a session during which the user operates the wearable.

Example 20: A method comprising (1) injecting a test signal into a skin surface of a user of an artificial reality system via a first electrode that interfaces with the skin surface of the user and is incorporated into a wearable donned by the user, (2) receiving the test signal via a second electrode that interfaces with the skin surface of the user and is incorporated into the wearable donned by the user, (3) measuring the test signal as received by the second electrode via a sensor communicatively coupled to the second electrode, and then (4) determining a current impedance of the skin surface based at least in part on (A) a known distance between the first electrode and the second electrode and (B) the measurement of the test signal as received by the second electrode.

The preceding description has been provided to enable others skilled in the art to best utilize various aspects of the exemplary embodiments disclosed herein. This exemplary description is not intended to be exhaustive or to be limited to any precise form disclosed. Many modifications and variations are possible without departing from the spirit and scope of the instant disclosure. The embodiments disclosed herein should be considered in all respects illustrative and not restrictive. Reference should be made to the appended claims and their equivalents in determining the scope of the instant disclosure.

Embodiments of the present disclosure may include or be implemented in conjunction with various types of artificial reality systems. Artificial reality is a form of reality that has been adjusted in some manner before presentation to a user, which may include, e.g., a virtual reality, an augmented reality, a mixed reality, a hybrid reality, or some combination and/or derivative thereof. Artificial reality content may include completely generated content or generated content combined with captured (e.g., real-world) content. The artificial reality content may include video, audio, haptic feedback, or some combination thereof, any of which may be presented in a single channel or in multiple channels (such as stereo video that produces a three-dimensional (3D) effect to the viewer). Additionally, in some embodiments, artificial reality may also be associated with applications, products, accessories, services, or some combination thereof, that are used to, e.g., create content in an artificial reality and/or are otherwise used in (e.g., to perform activities in) an artificial reality.

Artificial reality systems may be implemented in a variety of different form factors and configurations. Some artificial reality systems may be designed to work without near-eye displays (NEDs), an example of which is augmented reality system 1100 in FIG. 11. Other artificial reality systems may include an NED that also provides visibility into the real world (e.g., augmented reality system 1200 in FIG. 12) or that visually immerses a user in an artificial reality (e.g., virtual reality system 1300 in FIG. 13). While some artificial reality devices may be self-contained systems, other artificial reality devices may communicate and/or coordinate with external devices to provide an artificial reality experience to a user. Examples of such external devices include handheld controllers, mobile devices, desktop computers, devices worn by a user, devices worn by one or more other users, and/or any other suitable external system.

Figure 11:
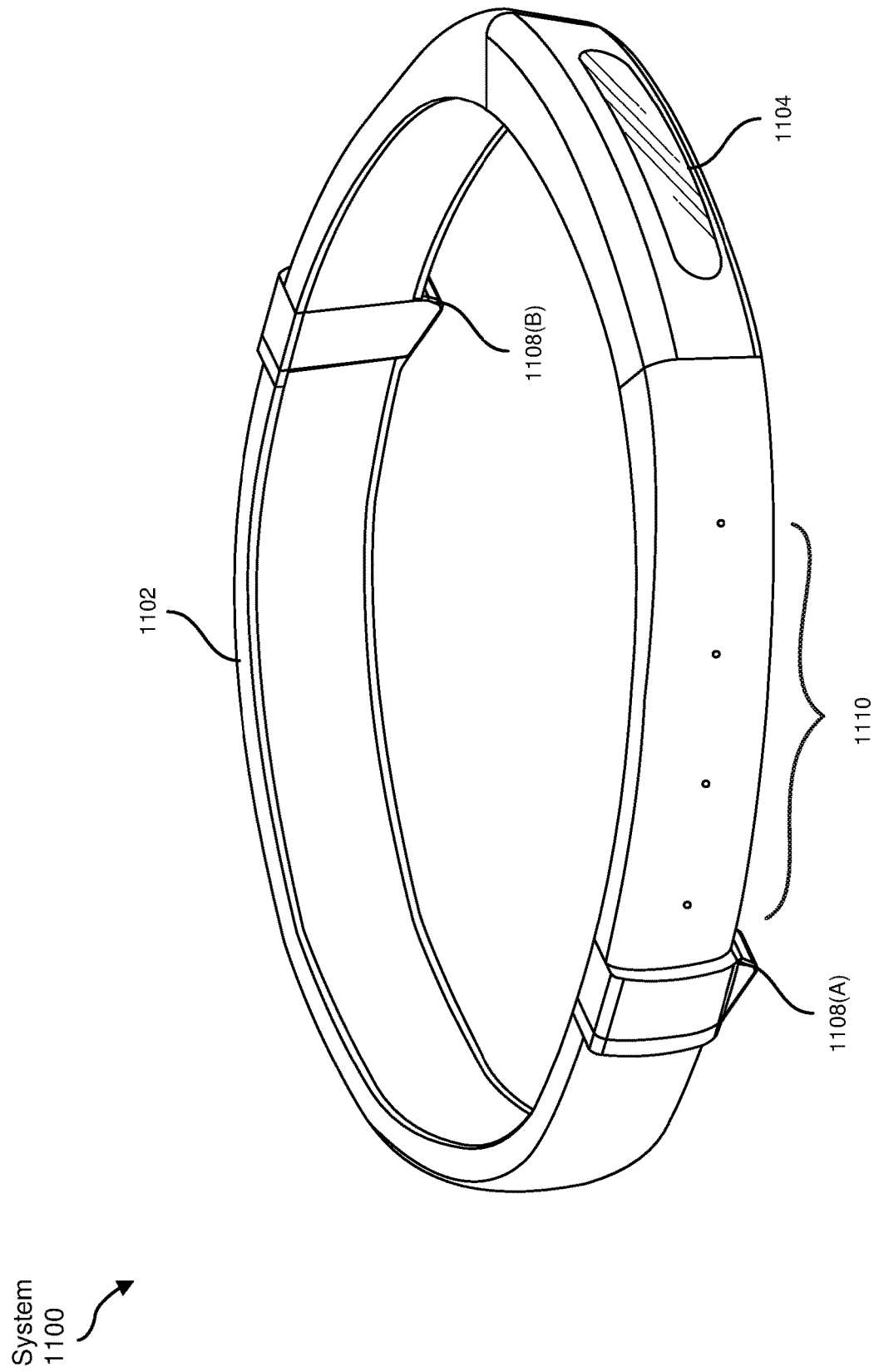
FIG. 11 is an illustration of an exemplary artificial reality headband that may be used in connection with embodiments of this disclosure.

Turning to FIG. 11, augmented reality system 1100 generally represents a wearable device dimensioned to fit about a body part (e.g., a head) of a user. As shown in FIG. 11, system 1100 may include a frame 1102 and a camera assembly 1104 that is coupled to frame 1102 and configured to gather information about a local environment by observing the local environment. Augmented reality system 1100 may also include one or more audio devices, such as output audio transducers 1108(A) and 1108(B) and input audio transducers 1110. Output audio transducers 1108(A) and 1108(B) may provide audio feedback and/or content to a user, and input audio transducers 1110 may capture audio in a user's environment.

As shown, augmented reality system 1100 may not necessarily include an NED positioned in front of a user's eyes. Augmented reality systems without NEDs may take a variety of forms, such as head bands, hats, hair bands, belts, watches, wrist bands, ankle bands, rings, neckbands, necklaces, chest bands, eyewear frames, and/or any other suitable type or form of apparatus. While augmented reality system 1100 may not include an NED, augmented reality system 1100 may include other types of screens or visual feedback devices (e.g., a display screen integrated into a side of frame 1102).

Figure 12:
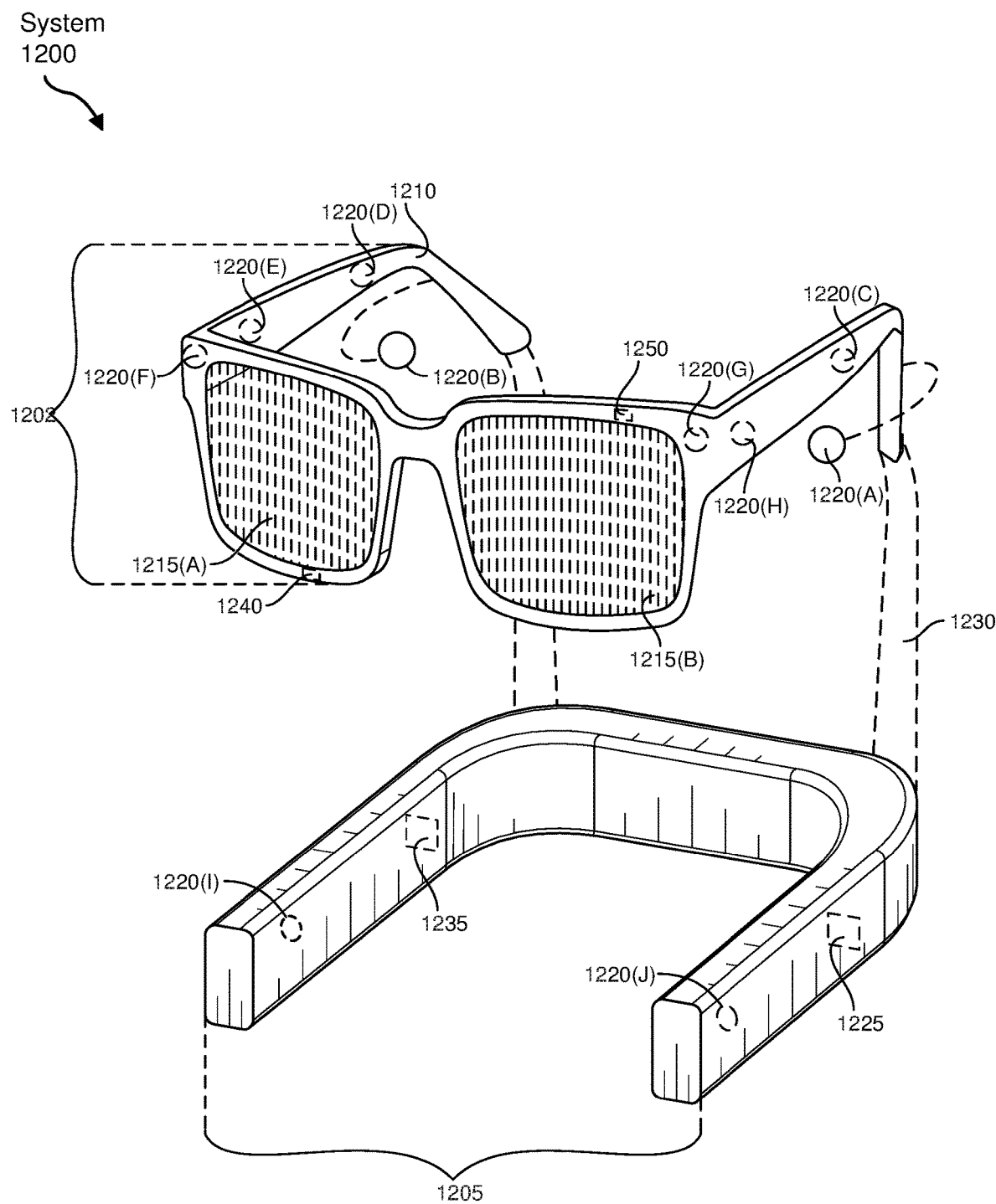
FIG. 12 is an illustration of exemplary augmented reality glasses that may be used in connection with embodiments of this disclosure.

The embodiments discussed in this disclosure may also be implemented in augmented reality systems that include one or more NEDs. For example, as shown in FIG. 12, augmented reality system 1200 may include an eyewear device 1202 with a frame 1210 configured to hold a left display device 1215(A) and a right display device 1215(B) in front of a user's eyes. Display devices 1215(A) and 1215(B) may act together or independently to present an image or series of images to a user. While augmented reality system 1200 includes two displays, embodiments of this disclosure may be implemented in augmented reality systems with a single NED or more than two NEDs.

In some embodiments, augmented reality system 1200 may include one or more sensors, such as sensor 1240. Sensor 1240 may generate measurement signals in response to motion of augmented reality system 1200 and may be located on substantially any portion of frame 1210. Sensor 1240 may represent a position sensor, an inertial measurement unit (IMU), a depth camera assembly, or any combination thereof. In some embodiments, augmented reality system 1200 may or may not include sensor 1240 or may include more than one sensor. In embodiments in which sensor 1240 includes an IMU, the IMU may generate calibration data based on measurement signals from sensor 1240. Examples of sensor 1240 may include, without limitation, accelerometers, gyroscopes, magnetometers, other suitable types of sensors that detect motion, sensors used for error correction of the IMU, or some combination thereof.

Augmented reality system 1200 may also include a microphone array with a plurality of acoustic transducers 1220(A)-1220(J), referred to collectively as acoustic transducers 1220. Acoustic transducers 1220 may be transducers that detect air pressure variations induced by sound waves. Each acoustic transducer 1220 may be configured to detect sound and convert the detected sound into an electronic format (e.g., an analog or digital format). The microphone array in FIG. 2 may include, for example, ten acoustic transducers: 1220(A) and 1220(B), which may be designed to be placed inside a corresponding ear of the user, acoustic transducers 1220(C), 1220(D), 1220(E), 1220(F), 1220(G), and 1220(H), which may be positioned at various locations on frame 1210, and/or acoustic transducers 1220(I) and 1220(J), which may be positioned on a corresponding neckband 1205.

In some embodiments, one or more of acoustic transducers 1220(A)-(F) may be used as output transducers (e.g., speakers). For example, acoustic transducers 1220(A) and/or 1220(B) may be earbuds or any other suitable type of headphone or speaker.

The configuration of acoustic transducers 1220 of the microphone array may vary. While augmented reality system 1200 is shown in FIG. 12 as having ten acoustic transducers 1220, the number of acoustic transducers 1220 may be greater or less than ten. In some embodiments, using higher numbers of acoustic transducers 1220 may increase the amount of audio information collected and/or the sensitivity and accuracy of the audio information. In contrast, using a lower number of acoustic transducers 1220 may decrease the computing power required by an associated controller 1250 to process the collected audio information. In addition, the position of each acoustic transducer 1220 of the microphone array may vary. For example, the position of an acoustic transducer 1220 may include a defined position on the user, a defined coordinate on frame 1210, an orientation associated with each acoustic transducer 1220, or some combination thereof.

Acoustic transducers 1220(A) and 1220(B) may be positioned on different parts of the user's ear, such as behind the pinna or within the auricle or fossa. Or, there may be additional acoustic transducers 1220 on or surrounding the ear in addition to acoustic transducers 1220 inside the ear canal. Having an acoustic transducer 1220 positioned next to an ear canal of a user may enable the microphone array to collect information on how sounds arrive at the ear canal. By positioning at least two of acoustic transducers 1220 on either side of a user's head (e.g., as binaural microphones), augmented reality device 1200 may simulate binaural hearing and capture a 3D stereo sound field around about a user's head. In some embodiments, acoustic transducers 1220(A) and 1220(B) may be connected to augmented reality system 1200 via a wired connection 1230, and in other embodiments, acoustic transducers 1220(A) and 1220(B) may be connected to augmented reality system 1200 via a wireless connection (e.g., a Bluetooth connection). In still other embodiments, acoustic transducers 1220(A) and 1220(B) may not be used at all in conjunction with augmented reality system 1200.

Acoustic transducers 1220 on frame 1210 may be positioned along the length of the temples, across the bridge, above or below display devices 1215(A) and 1215(B), or some combination thereof. Acoustic transducers 1220 may be oriented such that the microphone array is able to detect sounds in a wide range of directions surrounding the user wearing the augmented reality system 1200. In some embodiments, an optimization process may be performed during manufacturing of augmented reality system 1200 to determine relative positioning of each acoustic transducer 1220 in the microphone array.

In some examples, augmented reality system 1200 may include or be connected to an external device (e.g., a paired device), such as neckband 1205. Neckband 1205 generally represents any type or form of paired device. Thus, the following discussion of neckband 1205 may also apply to various other paired devices, such as charging cases, smart watches, smart phones, wrist bands, other wearable devices, hand-held controllers, tablet computers, laptop computers and other external compute devices, etc.

As shown, neckband 1205 may be coupled to eyewear device 1202 via one or more connectors. The connectors may be wired or wireless and may include electrical and/or non-electrical (e.g., structural) components. In some cases, eyewear device 1202 and neckband 1205 may operate independently without any wired or wireless connection between them. While FIG. 12 illustrates the components of eyewear device 1202 and neckband 1205 in example locations on eyewear device 1202 and neckband 1205, the components may be located elsewhere and/or distributed differently on eyewear device 1202 and/or neckband 1205. In some embodiments, the components of eyewear device 1202 and neckband 1205 may be located on one or more additional peripheral devices paired with eyewear device 1202, neckband 1205, or some combination thereof.

Pairing external devices, such as neckband 1205, with augmented reality eyewear devices may enable the eyewear devices to achieve the form factor of a pair of glasses while still providing sufficient battery and computation power for expanded capabilities. Some or all of the battery power, computational resources, and/or additional features of augmented reality system 1200 may be provided by a paired device or shared between a paired device and an eyewear device, thus reducing the weight, heat profile, and form factor of the eyewear device overall while still retaining desired functionality. For example, neckband 1205 may allow components that would otherwise be included on an eyewear device to be included in neckband 1205 since users may tolerate a heavier weight load on their shoulders than they would tolerate on their heads. Neckband 1205 may also have a larger surface area over which to diffuse and disperse heat to the ambient environment. Thus, neckband 1205 may allow for greater battery and computation capacity than might otherwise have been possible on a stand-alone eyewear device. Since weight carried in neckband 1205 may be less invasive to a user than weight carried in eyewear device 1202, a user may tolerate wearing a lighter eyewear device and carrying or wearing the paired device for greater lengths of time than a user would tolerate wearing a heavy stand-alone eyewear device, thereby enabling users to more fully incorporate artificial reality environments into their day-to-day activities.

Neckband 1205 may be communicatively coupled with eyewear device 1202 and/or to other devices. These other devices may provide certain functions (e.g., tracking, localizing, depth mapping, processing, storage, etc.) to augmented reality system 1200. In the embodiment of FIG. 12, neckband 1205 may include two acoustic transducers (e.g., 1220(1) and 1220(J)) that are part of the microphone array (or potentially form their own microphone subarray). Neckband 1205 may also include a controller 1225 and a power source 1235.

Acoustic transducers 1220(1) and 1220(J) of neckband 1205 may be configured to detect sound and convert the detected sound into an electronic format (analog or digital). In the embodiment of FIG. 12, acoustic transducers 1220(1) and 1220(J) may be positioned on neckband 1205, thereby increasing the distance between the neckband acoustic transducers 1220(1) and 1220(J) and other acoustic transducers 1220 positioned on eyewear device 1202. In some cases, increasing the distance between acoustic transducers 1220 of the microphone array may improve the accuracy of beam-forming performed via the microphone array. For example, if a sound is detected by acoustic transducers 1220(C) and 1220(D) and the distance between acoustic transducers 1220(C) and 1220(D) is greater than, e.g., the distance between acoustic transducers 1220(D) and 1220(E), the determined source location of the detected sound may be more accurate than if the sound had been detected by acoustic transducers 1220(D) and 1220(E).

Controller 1225 of neckband 1205 may process information generated by the sensors on neckband 1205 and/or augmented reality system 1200. For example, controller

1225 may process information from the microphone array that describes sounds detected by the microphone array. For each detected sound, controller 1225 may perform a direction-of-arrival (DOA) estimation to estimate a direction from which the detected sound arrived at the microphone array. As the microphone array detects sounds, controller 1225 may populate an audio data set with the information. In embodiments in which augmented reality system 1200 includes an inertial measurement unit, controller 1225 may compute all inertial and spatial calculations from the IMU located on eyewear device 1202. A connector may convey information between augmented reality system 1200 and neckband 1205 and between augmented reality system 1200 and controller 1225. The information may be in the form of optical data, electrical data, wireless data, or any other transmittable data form. Moving the processing of information generated by augmented reality system 1200 to neckband 1205 may reduce weight and heat in eyewear device 1202, making it more comfortable to the user.

Power source 1235 in neckband 1205 may provide power to eyewear device 1202 and/or to neckband 1205. Power source 1235 may include, without limitation, lithium ion batteries, lithium-polymer batteries, primary lithium batteries, alkaline batteries, or any other form of power storage. In some cases, power source 1235 may be a wired power source. Including power source 1235 on neckband 1205 instead of on eyewear device 1202 may help better distribute the weight and heat generated by power source 1235.

As noted, some artificial reality systems may, instead of blending an artificial reality with actual reality, substantially replace one or more of a user's sensory perceptions of the real world with a virtual experience. One example of this type of system is a head-worn display system, such as virtual reality system 1300 in FIG. 13, that mostly or completely covers a user's field of view. Virtual reality system 1300 may include a front rigid body 1302 and a band 1304 shaped to fit around a user's head. Virtual reality system 1300 may also include output audio transducers 1306(A) and 1306(B). Furthermore, while not shown in FIG. 13, front rigid body 1302 may include one or more electronic elements, including one or more electronic displays, one or more inertial measurement units (IMUS), one or more tracking emitters or detectors, and/or any other suitable device or system for creating an artificial reality experience.

Artificial reality systems may include a variety of types of visual feedback mechanisms. For example, display devices in augmented reality system 1200 and/or virtual reality system 1300 may include one or more liquid crystal displays (LCDs), light emitting diode (LED) displays, organic LED (OLED) displays, and/or any other suitable type of display screen. Artificial reality systems may include a single display screen for both eyes or may provide a display screen for each eye, which may allow for additional flexibility for varifocal adjustments or for correcting a user's refractive error. Some artificial reality systems may also include optical subsystems having one or more lenses (e.g., conventional concave or convex lenses, Fresnel lenses, adjustable liquid lenses, etc.) through which a user may view a display screen.

In addition to or instead of using display screens, some artificial reality systems may include one or more projection systems. For example, display devices in augmented reality system 1200 and/or virtual reality system 1300 may include micro-LED projectors that project light (using, e.g., a waveguide) into display devices, such as clear combiner lenses that allow ambient light to pass through. The display devices may refract the projected light toward a user's pupil and may enable a user to simultaneously view both artificial reality content and the real world. Artificial reality systems may also be configured with any other suitable type or form of image projection system.

Artificial reality systems may also include various types of computer vision components and subsystems. For example, augmented reality system 1100, augmented reality system 1200, and/or virtual reality system 1300 may include one or more optical sensors, such as two-dimensional (2D) or 3D cameras, time-of-flight depth sensors, single-beam or sweeping laser rangefinders, 3D LiDAR sensors, and/or any other suitable type or form of optical sensor. An artificial reality system may process data from one or more of these sensors to identify a location of a user, to map the real world, to provide a user with context about real-world surroundings, and/or to perform a variety of other functions.

Artificial reality systems may also include one or more input and/or output audio transducers. In the examples shown in FIGS. 11 and 13, output audio transducers 1108(A), 1108(B), 1306(A), and 1306(B) may include voice coil speakers, ribbon speakers, electrostatic speakers, piezoelectric speakers, bone conduction transducers, cartilage conduction transducers, and/or any other suitable type or form of audio transducer. Similarly, input audio transducers 1110 may include condenser microphones, dynamic microphones, ribbon microphones, and/or any other type or form of input transducer. In some embodiments, a single transducer may be used for both audio input and audio output.

Figure 13:
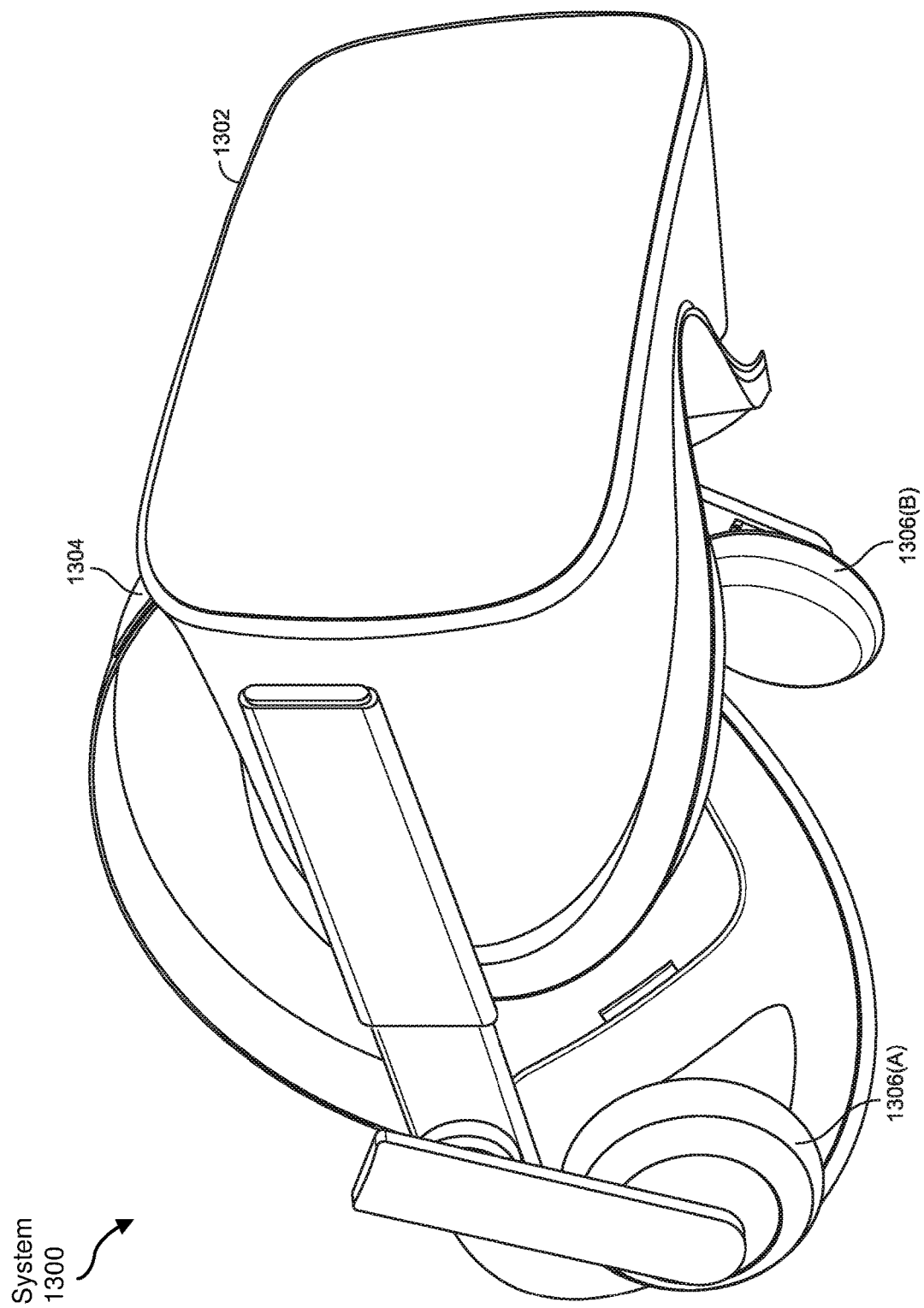
FIG. 13 is an illustration of an exemplary virtual reality headset that may be used in connection with embodiments of this disclosure.

While not shown in FIGS. 11-13, artificial reality systems may include tactile (i.e., haptic) feedback systems, which may be incorporated into headwear, gloves, body suits, handheld controllers, environmental devices (e.g., chairs, floormats, etc.), and/or any other type of device or system. Haptic feedback systems may provide various types of cutaneous feedback, including vibration, force, traction, texture, and/or temperature. Haptic feedback systems may also provide various types of kinesthetic feedback, such as motion and compliance. Haptic feedback may be implemented using motors, piezoelectric actuators, fluidic systems, and/or a variety of other types of feedback mechanisms. Haptic feedback systems may be implemented independent of other artificial reality devices, within other artificial reality devices, and/or in conjunction with other artificial reality devices.

By providing haptic sensations, audible content, and/or visual content, artificial reality systems may create an entire virtual experience or enhance a user's real-world experience in a variety of contexts and environments. For instance, artificial reality systems may assist or extend a user's perception, memory, or cognition within a particular environment. Some systems may enhance a user's interactions with other people in the real world or may enable more immersive interactions with other people in a virtual world. Artificial reality systems may also be used for educational purposes (e.g., for teaching or training in schools, hospitals, government organizations, military organizations, business enterprises, etc.), entertainment purposes (e.g., for playing video games, listening to music, watching video content, etc.), and/or for accessibility purposes (e.g., as hearing aids, visuals aids, etc.). The embodiments disclosed herein may enable or enhance a user's artificial reality experience in one or more of these contexts and environments and/or in other contexts and environments.

As noted, artificial reality systems 1100, 1200, and 1300 may be used with a variety of other types of devices to provide a more compelling artificial reality experience. These devices may be haptic interfaces with transducers that provide haptic feedback and/or that collect haptic information about a user's interaction with an environment. The artificial reality systems disclosed herein may include various types of haptic interfaces that detect or convey various types of haptic information, including tactile feedback (e.g., feedback that a user detects via nerves in the skin, which may also be referred to as cutaneous feedback) and/or kinesthetic feedback (e.g., feedback that a user detects via receptors located in muscles, joints, and/or tendons).

Figure 14:
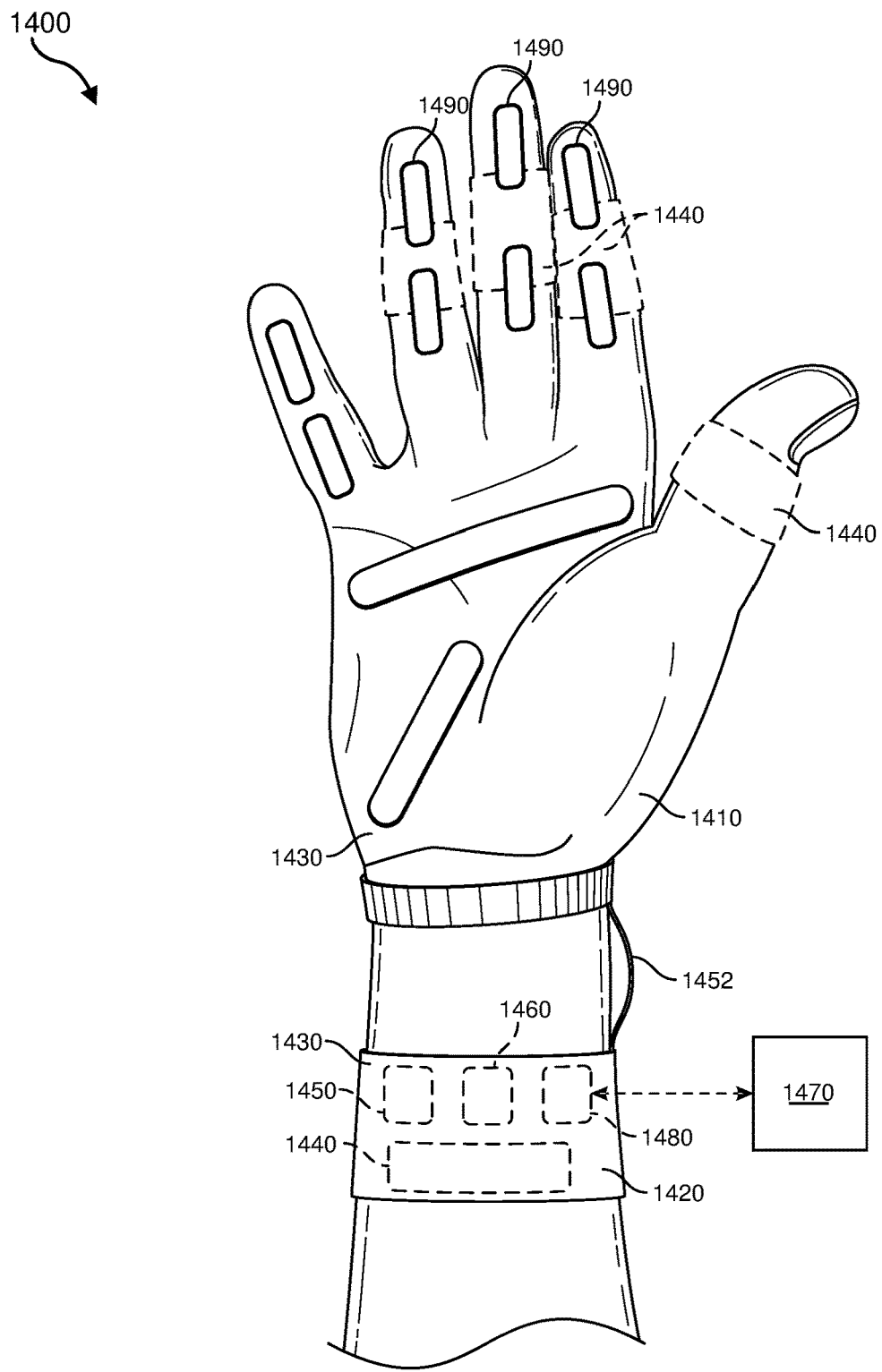
FIG. 14 is an illustration of exemplary haptic devices that may be used in connection with embodiments of this disclosure.

Haptic feedback may be provided by interfaces positioned within a user's environment (e.g., chairs, tables, floors, etc.) and/or interfaces on articles that may be worn or carried by a user (e.g., gloves, wristbands, etc.). As an example, FIG. 14 illustrates a vibrotactile system 1400 in the form of a wearable glove (haptic device 1410) and wristband (haptic device 1420). Haptic device 1410 and haptic device 1420 are shown as examples of wearable devices that include a flexible, wearable textile material 1430 that is shaped and configured for positioning against a user's hand and wrist, respectively. This disclosure also includes vibrotactile systems that may be shaped and configured for positioning against other human body parts, such as a finger, an arm, a head, a torso, a foot, or a leg. By way of example and not limitation, vibrotactile systems according to various embodiments of the present disclosure may also be in the form of a glove, a headband, an armband, a sleeve, a head covering, a sock, a shirt, or pants, among other possibilities. In some examples, the term "textile" may include any flexible, wearable material, including woven fabric, non-woven fabric, leather, cloth, a flexible polymer material, composite materials, etc.

One or more vibrotactile devices 1440 may be positioned at least partially within one or more corresponding pockets formed in textile material 1430 of vibrotactile system 1400. Vibrotactile devices 1440 may be positioned in locations to provide a vibrating sensation (e.g., haptic feedback) to a user of vibrotactile system 1400. For example, vibrotactile devices 1440 may be positioned to be against the user's finger(s), thumb, or wrist, as shown in FIG. 14. Vibrotactile devices 1440 may, in some examples, be sufficiently flexible to conform to or bend with the user's corresponding body part(s).

A power source 1450 (e.g., a battery) for applying a voltage to the vibrotactile devices 1440 for activation thereof may be electrically coupled to vibrotactile devices 1440, such as via conductive wiring 1452. In some examples, each of vibrotactile devices 1440 may be independently electrically coupled to power source 1450 for individual activation. In some embodiments, a processor 1460 may be operatively coupled to power source 1450 and configured (e.g., programmed) to control activation of vibrotactile devices 1440.

Vibrotactile system 1400 may be implemented in a variety of ways. In some examples, vibrotactile system 1400 may be a standalone system with integral subsystems and components for operation independent of other devices and systems. As another example, vibrotactile system 1400 may be configured for interaction with another device or system 1470. For example, vibrotactile system 1400 may, in some examples, include a communications interface 1480 for receiving and/or sending signals to the other device or system 1470. The other device or system 1470 may be a mobile device, a gaming console, an artificial reality (e.g., virtual reality, augmented reality, mixed reality) device, a personal computer, a tablet computer, a network device (e.g., a modem, a router, etc.), a handheld controller, etc. Communications interface 1480 may enable communications between vibrotactile system 1400 and the other device or system 1470 via a wireless (e.g., Wi-Fi, Bluetooth, cellular, radio, etc.) link or a wired link. If present, communications interface 1480 may be in communication with processor 1460, such as to provide a signal to processor 1460 to activate or deactivate one or more of the vibrotactile devices 1440.

Vibrotactile system 1400 may optionally include other subsystems and components, such as touch-sensitive pads 1490, pressure sensors, motion sensors, position sensors, lighting elements, and/or user interface elements (e.g., an on/off button, a vibration control element, etc.). During use, vibrotactile devices 1440 may be configured to be activated for a variety of different reasons, such as in response to the user's interaction with user interface elements, a signal from the motion or position sensors, a signal from the touch-sensitive pads 1490, a signal from the pressure sensors, a signal from the other device or system 1470, etc.

Although power source 1450, processor 1460, and communications interface 1480 are illustrated in FIG. 14 as being positioned in haptic device 1420, the present disclosure is not so limited. For example, one or more of power source 1450, processor 1460, or communications interface 1480 may be positioned within haptic device 1410 or within another wearable textile.

Figure 15:
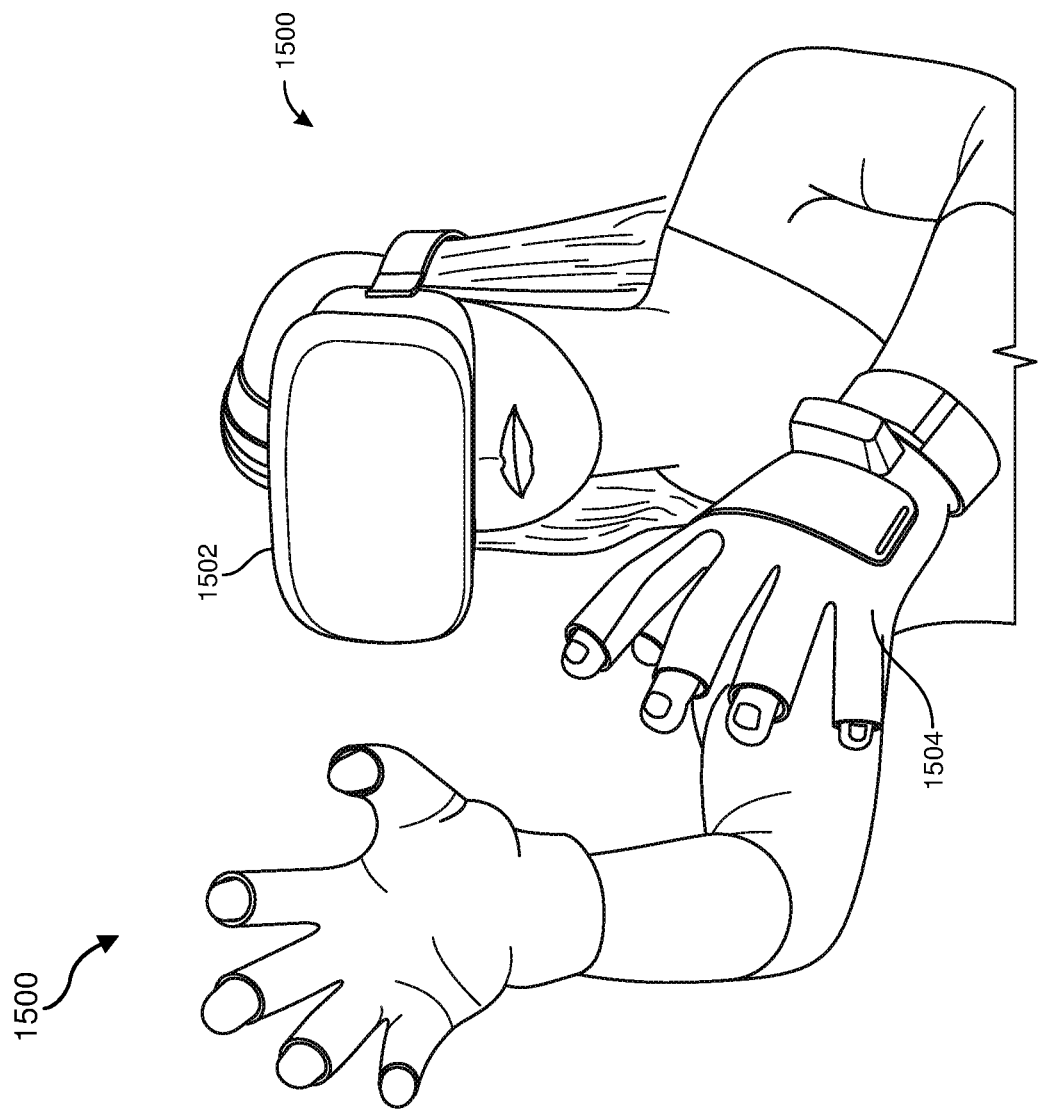
FIG. 15 is an illustration of an exemplary virtual reality environment according to embodiments of this disclosure.

Haptic wearables, such as those shown in and described in connection with FIG. 14, may be implemented in a variety of types of artificial reality systems and environments. FIG. 15 shows an example artificial reality environment 1500 including one head-mounted virtual reality display and two haptic devices (i.e., gloves), and in other embodiments any number and/or combination of these components and other components may be included in an artificial reality system. For example, in some embodiments there may be multiple head-mounted displays each having an associated haptic device, with each head-mounted display and each haptic device communicating with the same console, portable computing device, or other computing system.

Head-mounted display 1502 generally represents any type or form of virtual reality system, such as virtual reality system 1000 in FIG. 10. Haptic device 1504 generally represents any type or form of wearable device, worn by a use of an artificial reality system, that provides haptic feedback to the user to give the user the perception that he or she is physically engaging with a virtual object. In some embodiments, haptic device 1504 may provide haptic feedback by applying vibration, motion, and/or force to the user. For example, haptic device 1504 may limit or augment a user's movement. To give a specific example, haptic device 1504 may limit a user's hand from moving forward so that the user has the perception that his or her hand has come in physical contact with a virtual wall. In this specific example, one or more actuators within the haptic advice may achieve the physical-movement restriction by pumping fluid into an inflatable bladder of the haptic device. In some examples, a user may also use haptic device 1504 to send action requests to a console. Examples of action requests include, without limitation, requests to start an application and/or end the application and/or requests to perform a particular action within the application.

Figure 16:
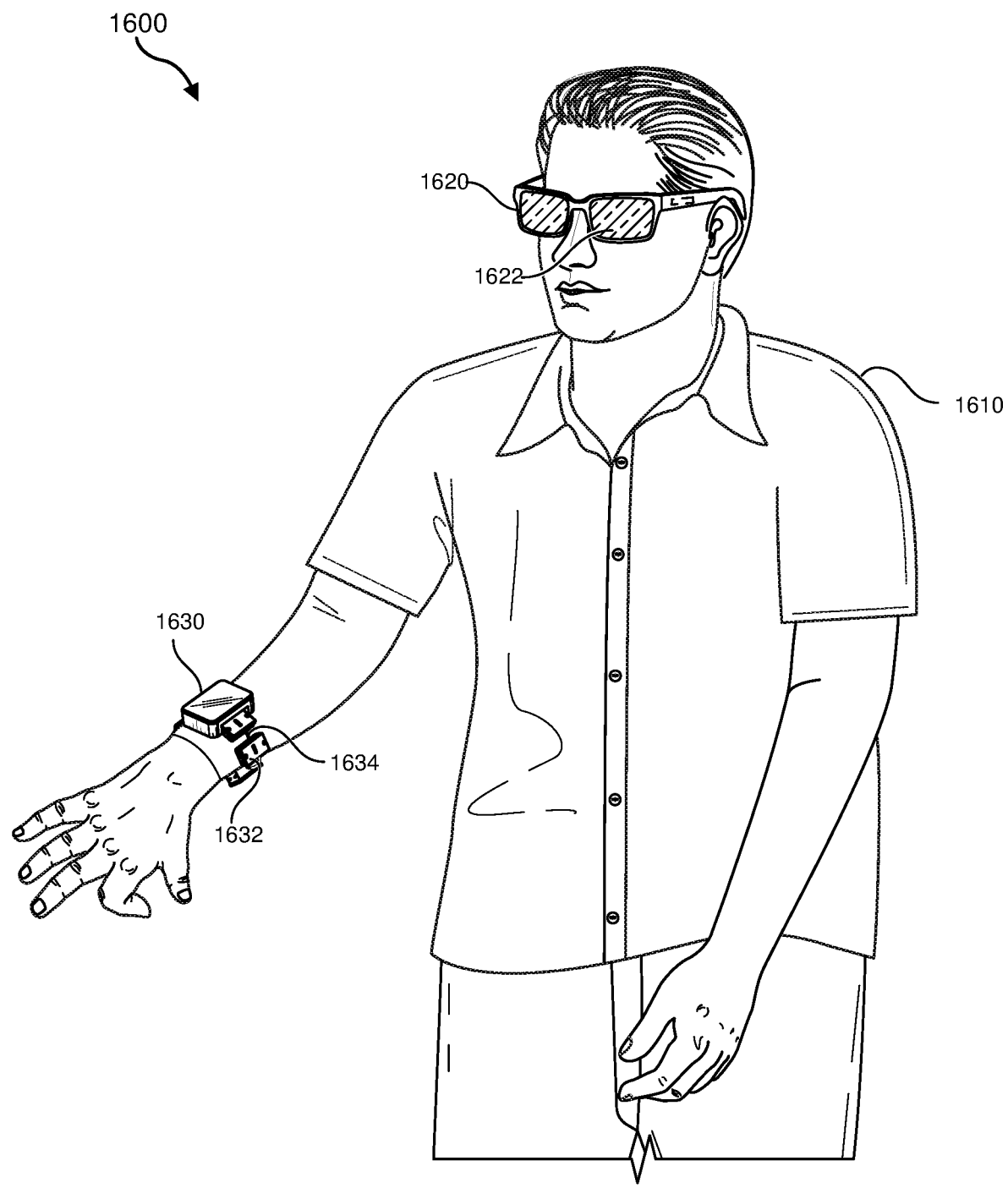
FIG. 16 is an illustration of an exemplary augmented reality environment according to embodiments of this disclosure.

While haptic interfaces may be used with virtual reality systems, as shown in FIG. 15, haptic interfaces may also be used with augmented reality systems, as shown in FIG. 16. FIG. 16 is a perspective view a user 1610 interacting with an augmented reality system 1600. In this example, user 1610 may wear a pair of augmented reality glasses 1620 that have one or more displays 1622 and that are paired with a haptic device 1630. Haptic device 1630 may be a wristband that includes a plurality of band elements 1632 and a tensioning mechanism 1634 that connects band elements 1632 to one another.

One or more of band elements 1632 may include any type or form of actuator suitable for providing haptic feedback. For example, one or more of band elements 1632 may be configured to provide one or more of various types of cutaneous feedback, including vibration, force, traction, texture, and/or temperature. To provide such feedback, band elements 1632 may include one or more of various types of actuators. In one example, each of band elements 1632 may include a vibrotactor (e.g., a vibrotactile actuator) configured to vibrate in unison or independently to provide one or more of various types of haptic sensations to a user. Alternatively, only a single band element or a subset of band elements may include vibrotactors.

Haptic devices 1410, 1420, 1504, and 1630 may include any suitable number and/or type of haptic transducer, sensor, and/or feedback mechanism. For example, haptic devices 1410, 1420, 1504, and 1630 may include one or more mechanical transducers, piezoelectric transducers, and/or fluidic transducers. Haptic devices 1410, 1420, 1504, and 1630 may also include various combinations of different types and forms of transducers that work together or independently to enhance a user's artificial-reality experience. In one example, each of band elements 1632 of haptic device 1630 may include a vibrotactor (e.g., a vibrotactile actuator) configured to vibrate in unison or independently to provide one or more of various types of haptic sensations to a user.

The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed. The various exemplary methods described and/or illustrated herein may also omit one or more of the steps described or illustrated herein or include additional steps in addition to those disclosed.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of." Finally, for ease of use, the terms "including" and "having" (and their derivatives), as used in the specification and claims, are interchangeable with and have the same meaning as the word "comprising."

What is claimed is:

1. A wearable comprising:
    a plurality of electrodes dimensioned to interface with a skin surface of a user of an artificial reality system, wherein the electrodes are spaced a known distance from one another;
    a signal generator communicatively coupled to one of the electrodes, wherein the signal generator injects a test signal into the skin surface of the user via the one of the electrodes;
    a resistor of known constant resistance that forms part of an impedance divider circuit, wherein:
        the resistor of known constant resistance is electrically coupled to another one of the electrodes; and
        the impedance divider circuit includes a current impedance of the skin surface in series with the resistor of known constant resistance;
    at least one sensor communicatively coupled to the another one of the electrodes, wherein the sensor measures the test signal as received by the another one of the electrodes via the impedance divider circuit; and
    at least one processing device communicatively coupled to the sensor, wherein the processing device:
        determines the current impedance of the skin surface based at least in part on the known distance between the electrodes and the measurement of the test signal as received by the another one of the electrodes; and
        calibrates the wearable to account for the current impedance of the skin surface by applying the current impedance of the skin surface to a model that represents the skin surface to facilitate measuring distances from the electrodes to body contact on the user.

2. The wearable of claim 1, wherein the test signal injected into the skin surface of the user has at least one of:
    a known frequency;
    a known voltage level; or
    a known current level.

3. The wearable of claim 1, wherein the test signal injected into the skin surface of the user has at least one of:
    a frequency within a range of 10 kilohertz and 100 megahertz;
    an amplitude within a range of 500 millivolts and 5 volts; or
    an electric current within a range of 100 microamps and 10 milliamps.

4. The wearable of claim 1, wherein the processing device:
    identifies one or more characteristics of the measurement of the test signal as received by the another one of the electrodes; and
    determines, based at least in part on the characteristics of the measurement of the test signal, the current impedance of the skin surface.

5. The wearable of claim 4, wherein the characteristics of the measurement of the test signal comprise at least one of:
    a strength of the test signal as received by the another one of the electrodes;
    an envelope of the test signal as received by the another one of the electrodes;
    a frequency of the test signal as received by the another one of the electrodes; or
    an amplitude of the test signal as received by the another one of the electrodes.

6. The wearable of claim 1, wherein the processing device automatically self-calibrates at a beginning of a session during which the user operates the wearable.

7. The wearable of claim 1, wherein:
    the signal generator injects a plurality of test signals into the skin surface of the user via the one of the electrodes, wherein the plurality of test signals have varying frequencies;
    the sensor measures the plurality of test signals as received by the another one of the electrodes; and
    the processing device:
        analyzes a frequency response of the skin surface based at least in part on the measurements of the test signals as received by the another one of the electrodes; and
        estimates the current impedance of the skin surface based at least in part on the frequency response of the skin surface.

8. The wearable of claim 1, further comprising a fastener dimensioned to facilitate securing the wearable to a wrist of the user of the artificial reality system;
wherein:
the skin surface comprises a wrist area of the user; and
the processing device:
implements an additional model that represents a relationship between the wrist area of the user and a hand of the user; and
estimates a current impedance of an additional skin surface between the wrist area of the user and the hand of the user.

9. The wearable of claim 1, further comprising a fastener that secures the wearable proximate to a first hand of the user of the artificial reality system; and
wherein:
the electrodes receive a radio frequency signal emitted by a transmitter incorporated in an additional wearable secured proximate to a second hand of the user as the second hand makes physical contact with the first hand;
the sensor is communicatively coupled to the electrodes and measures a signal strength of the radio frequency signal as received by the electrodes; and
the processing device determines a touch point that represents a relative location at which the second hand makes physical contact with the first hand based at least in part on:
the current impedance of the skin surface; and
the signal strength of the radio frequency signal as received by the electrodes.

10. The wearable of claim 9, wherein the processing device facilitates modifying at least one virtual component of the artificial reality system to account for the touch point.

11. A system comprising:
a plurality of electrodes dimensioned to interface with a skin surface of a user of an artificial reality system, wherein the electrodes are spaced a known distance from one another;
a signal generator communicatively coupled to one of the electrodes, wherein the signal generator injects a test signal into the skin surface of the user via the one of the electrodes;
a resistor of known constant resistance that forms part of an impedance divider circuit, wherein:
the resistor of known constant resistance is electrically coupled to another one of the electrodes; and
the impedance divider circuit includes a current impedance of the skin surface in series with the resistor of known constant resistance;
at least one sensor communicatively coupled to the another one of the electrodes, wherein the sensor measures the test signal as received by the another one of the electrodes via the impedance divider circuit; and
at least one processing device communicatively coupled to the sensor, wherein the processing device:
determines the current impedance of the skin surface based at least in part on the known distance between the electrodes and the measurement of the test signal as received by the another one of the electrodes; and
calibrates a wearable to account for the current impedance of the skin surface by applying the current impedance of the skin surface to a model that represents the skin surface to facilitate measuring distances from the electrodes to body contact on the user.

12. The system of claim 11, wherein the test signal injected into the skin surface of the user has at least one of:
a known frequency;
a known voltage level; or
a known current level.

13. The system of claim 11, wherein the test signal injected into the skin surface of the user has at least one of:
a frequency within a range of 10 kilohertz and 100 megahertz;
an amplitude within a range of 500 millivolts and 5 volts; or
an electric current within a range of 100 microamps and 10 milliamps.

14. The system of claim 11, wherein the processing device:
identifies one or more characteristics of the measurement of the test signal as received by the another one of the electrodes; and
determines, based at least in part on the characteristics of the measurement of the test signal, the current impedance of the skin surface.

15. The system of claim 14, wherein the characteristics of the measurement of the test signal comprise at least one of:
a strength of the test signal as received by the another one of the electrodes;
an envelope of the test signal as received by the another one of the electrodes;
a frequency of the test signal as received by the another one of the electrodes; or
an amplitude of the test signal as received by the another one of the electrodes.

16. The system of claim 11, wherein the processing device automatically self-calibrates at a beginning of a session during which the user operates the system.

17. A method comprising:
injecting a test signal into a skin surface of a user of an artificial reality system via a first electrode that interfaces with the skin surface of the user and is incorporated into a wearable donned by the user;
receiving the test signal via a second electrode that interfaces with the skin surface of the user and is incorporated into the wearable donned by the user, the second electrode being electrically coupled to a resistor of known constant resistance that forms part of an impedance divider circuit, wherein the impedance divider circuit includes a current impedance of the skin surface in series with the resistor of known constant resistance;
measuring, by a sensor communicatively coupled to the second electrode, the test signal as received by the second electrode via the impedance divider circuit;
determining a current impedance of the skin surface based at least in part on:
a known distance between the first electrode and the second electrode; and
the measurement of the test signal as received by the second electrode; and
calibrating the wearable to account for the current impedance of the skin surface by applying the current impedance of the skin surface to a model that represents the skin surface to facilitate measuring distances from the electrodes to body contact of the user.

18. The wearable of claim 1, wherein the processing device determines a distance to a touch point relative to the electrodes based at least in part on:
the model that represents the skin surface;
the current impedance of the skin surface; and a signal strength of a radio frequency signal received by the electrodes.

\* \* \* \* \*